United States Patent
Bredehorst et al.

(10) Patent No.: US 7,696,323 B2
(45) Date of Patent: Apr. 13, 2010

(54) BIVALENT IGY ANTIBODY CONSTRUCTS FOR DIAGNOSTIC AND THERAPEUTIC APPLICATIONS

(75) Inventors: Reinhard Bredehorst, Hamburg (DE); Kerstin Greunke, Hamburg (DE); Thomas Grunwald, Hamburg (DE); Edzard Spillner, Hamburg (DE)

(73) Assignee: PLS-Design GmbH, Hamburg (DE)

( * ) Notice: Subject to any disclaimer, the term of this patent is extended or adjusted under 35 U.S.C. 154(b) by 0 days.

(21) Appl. No.: 11/510,329

(22) Filed: Aug. 25, 2006

(65) Prior Publication Data
US 2007/0141049 A1 Jun. 21, 2007

(30) Foreign Application Priority Data
Aug. 26, 2005 (EP) ................... 05018607

(51) Int. Cl.
C07K 16/00 (2006.01)
A61K 39/395 (2006.01)
(52) U.S. Cl. .............. 530/387.3; 530/387.1; 424/130.1; 424/133.1
(58) Field of Classification Search .................... None
See application file for complete search history.

(56) References Cited

U.S. PATENT DOCUMENTS 4,550,019 A 10/1985 Polson
2005/0221424 A1* 10/2005 Utku .......................... 435/69.1

OTHER PUBLICATIONS

Greunke et al. Journal of Biotechnology, 2006, 124:446-456.*
Ryabova et al. Nature Biotechnology, 1997, 15:79-84.*
Randolf et al. Recombinant Antibodies: Applications in Plant Science and Plant Pathology, 1999, Taylor & Francis Inc., Philadelphia PA, Chapter 4, pp. 57-60.*
Andris-Widhopf et al. Jim 2000 242:159-181.*
Andris-Widhopf J, Rader C, Steinberger P, Fuller R, Barbas CF 3rd. (2000) Methods for the generation of chicken monoclonal antibody fragments by phage display. J. Immunol. Methods, 242(1-2): 159-81.
Arbabi Ghahroudi M, Desmyter A, Wyns L, Hamers S, Muyldermans S. (1997) Selection and identification of single domain antibody fragments from camel heavy-chain antibodies. FEBS Letts., 414: 521-26.
Ashikari Y, Arata Y, Hamaguchi K. (1985) pH-induced unfolding of the constant fragment of the immunoglobulin light chain: effect of reduction of the intrachain disulfide bond. J. Biochem., 97(2): 517-28.
Baatrup G, Svehag SE, Jensenius JC. (1986) The attachment of serum- and plasma-derived C3 to solid-phase immune aggregates and its relation to complement-mediated solubilization of immune complexes. Scand. J. Immunol., 23(4): 397-406.
Barbas CF 3rd, Bain JD, Hoekstra DM, Lerner RA. (1992) Semisynthetic combinatorial antibody libraries: a chemical solution to the diversity problem. Proc. Natl. Acad. Sci. USA, 89(10): 4457-61.
Barbas CF 3rd, Collet TA, Amberg W, Roben P, Binley JM, Hoekstra D, Cababa D, Jones TM, Williamson RA, Pilkington GR, et al. (1993) Molecular profile of an antibody repsonse to HIV-1 as probed by combinatorial libraries. J. Mol. Biol., 230(3): 812-23.
Basu M, Hakimi J, Dharm E, Kondas JA, Tsien WH, Pilson RS, Lin P, Gilfillan A, Haring P, Braswell EH, et al. (1993) Purification and characterization of human recombinant IgE-Fc fragments that bind to the human high affinity IgE receptor. J. Biol. Chem., 268(18): 13118-27.
Benkirane R, Gottschalk MG, Jacques M, Dubreuil JD. (1998) Immunochemical characterization of an IgG-binding protein of Streptococcus suis. FEMS Immunol. Med. Microbiol., 20(2): 121-27.
Blum PM, Phelps DL, Ank BJ, Krantman HJ, Stiehm ER. (1981) Survival of oral human immune serum globulin in the gastrointestinal tract of low birth weight infants, Pediatr. Res., 15(9): 1256-60.
Bogstedt AK, Hammarström L, Robertson AK. (1997) Survival of immunoglobulins from different species through the gastrointestinal tract in healthy adult volunteers: implications for human therapy. Antimicrob. Agents Chemother., 41(10): 2320.
Bosacto LM, Stuart MC. (1986) Incidence and specificity of interference in two-site immunoassays. Clin. Chem., 32(8): 1491-95.
Boscato LM, Stuart MC.H (1988) Heterophilic antibodies: a problem for all immunoassays. Clin. Chem., 34(1): 27-33.
Campbell RD, Dodds AW, Proter RR. (1980) The binding of human complement component C4 to antibody-antigen aggregates. Biochem J., 189(1): 67-80.
Chambers RE, Whicher JT, Perry DE, Milford-Ward A, White PA, Fifield R. (1987) Overestimation of immunoglobulins in the presence of rheumatoid factor by kinetic immunonephelometry and rapid immunoturbidimetry. Ann. Clin. Biochem., 24(Pt 5): 520-24.
Clackson T, Hoogenboom HR, Griffiths AD, Winter G. (1991) Making antibody fragments using phage display libraries. Nature, 352(6336): 624-28.
Copelan EA, Bechtel TP, Klein JP, Klein JL, Tutschka P, Kapoor N, Featheringham NC, Avalos BR. (1994) Controlled trial of orally administered immunoglobulin following bone marrow transplantation. Bone Marrow Transplant., 13(1): 87-91.

(Continued)

Primary Examiner—Phillip Gambel
Assistant Examiner—Sharon Wen
(74) Attorney, Agent, or Firm—Ballard Spahr LLP

(57) ABSTRACT

This invention relates to the field of recombinant antibody technology. It provides novel recombinant IgY antibody constructs for diagnostic and therapeutical applications. The bivalent antibody constructs display a heterotetrameric or homodimeric format stabilized by disulfide bonds. The constant heavy chain domains $C_H2$-$C_H4$ are partly or completely of avian origin, whereas the $V_H$, $V_L$, $C_L$, and $C_H1$ domains as well as the hinge region may be of avian origin or derived from any other species. The invention allows to combine the advantages of IgY antibodies with those of established mammalian monoclonal antibodies. IgY antibody constructs comprising nonglycosylated IgY constant heavy chain domains allow to reduce unwanted interactions with C-type lectins, e.g., in human sera. Furthermore, chimeric IgY antibody containing mammalian $V_H$, $V_L$, $C_L$, and $C_H1$ domains as well as a mammalian hinge region provide a higher molecular stability than IgY antibodies in acidic conditions and, thereby, are especially suited for peroral therapeutic applications.

23 Claims, 19 Drawing Sheets

OTHER PUBLICATIONS

Figure 1:
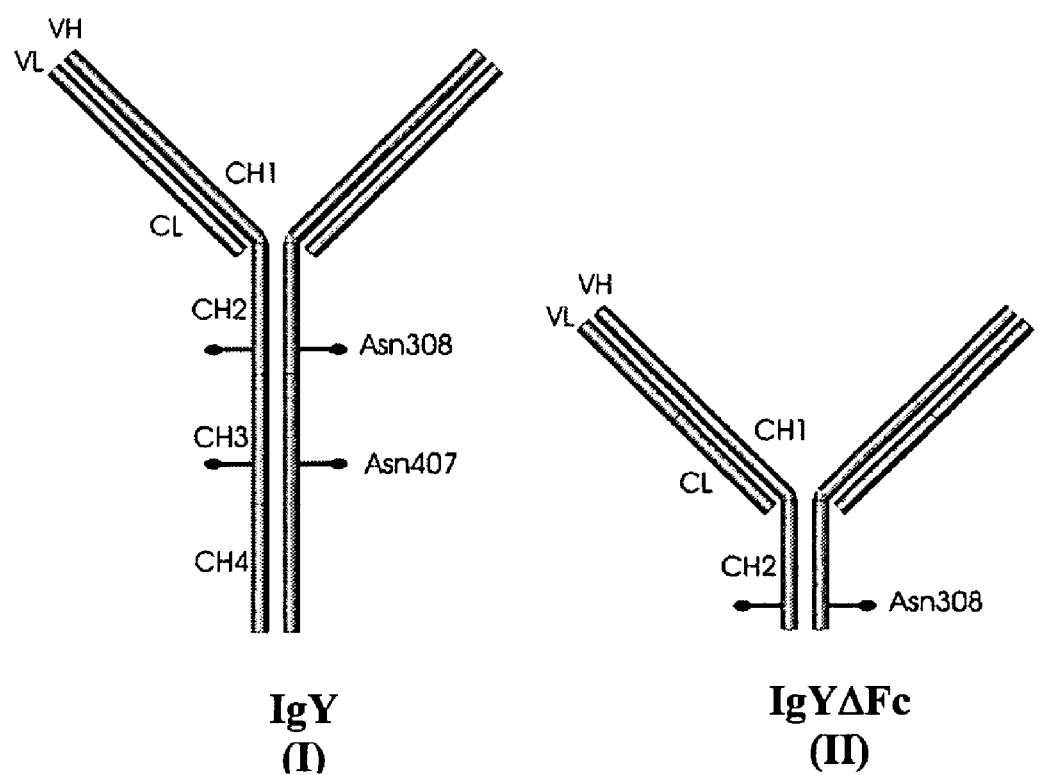

Davies EL, Smith JS, Birkett CR, Manser JM, Anderson-Dear DV, Young JR. (1995) Selection of specific phage-display antibodies using libraries derived from chicken immunoglobulin genes. J. Immunol. Methods, 186(1): 125-35.

Eibl MM, Wolf HM, Fürnkranz H, Rosenkranz A. (1988) Prevention of necrotizing enterocolitis in low-birth-weight infants by IgA-IgG feeding. N. Engl. J. Med., 319(1): 1-7.

Engström PE, Larsson A, Norhagen G, Smith CI, Sällberg M, Helgeland K, Hammarstöm L. (1993) Specificity and levels of oral and systemic antibodies to Actinobacillus actinomycetemcomitans. J. Clin. Periodontol., 20(10): 746-51.

Faith RE, Clem LW. (1973) Passive cutaneous anaphylaxis in the chicken. Biological fractionation of the mediating antibody population. Immunology, 25(1): 151-64.

Figdor CG, van Kooyk Y, Adema GJ. (2002) C-type lectin receptors on dendritic cells and Langerhans cells. Nat. Rev. Immunol., 2(2): 77-84.

Fischer M, Hlinak A. (2000) The lack of binding ability of staphylococcal protein A and streptococcal protein G to egg yolk immunoglobulins of different fowl species (short communication). Berl. Munch. Tierarztl. Wochenschr., 113(3): 94-96.

Geer LY, Domrachev M, Lipman DJ, Bryant SH. (2002) CDART: protein homology by domain architecture. Genome Res., 12(10): 1619-23.

Goto Y, Hamaguchi K. (1979) The role of the intrachain disulfide bond in the conformation and stability of the constant fragment of the immunoglobulin light chain. J. Biochem., 86(5): 1433-41.

Guss B, Eliasson M, Olsson A, Uhlén M, Frej AK, Jönvall H, Flock JI, Lindberg M. (1986) Structure of the IgG-binding regions of streptococcal protein G. EMBO J., 5(7): 1567-75.

Hendershot LM. (2004) The ER function BiP is a master regulator of ER function. Mt. Sinai J. Med., 71(5): 289-97.

Hendershot L, Wei J, Gaut J, Melnick J, Aviel S, Argon Y. (1996) Inhibition of immunoglobulin folding and secretin by dominant negative BiP ATPase mutants. Proc. Natl. Acad. Sci. USA, 93(11): 5269-74.

Hendershot L, Bole D, Köhler G, Kearney JF. (1987) Assembly and secretion of heavy chains that do not associate posttranslationally with immunoglobulin heavy chain-binding protein. J. Cell Biol., 104(3): 761-67.

Hilpert H, Brüssow H, Mietens C, Sidoti J, Lerner L, Werchau H. (1987) Use of bovine milk concentrate containing antibody to rotavirus to treat rotavirus gastroenteritis in infants. J. Infect. Dis., 156(1): 158-66.

Hoffman WL, Ruggles AO, Tabarya D. (1996) Chicken anti-protein A prevents *Staphylococcus aureus* protein A from binding to human and rabbit IgG in immunoassays and eliminates most false positive results. J. Immunol. Methods, 198(1): 67-77.

Holliger P, Winter G. (1997) Diabodies: small bispecific antibody fragments. Cancer Immunol. Immunother., 45(3-4): 128-30.

Hoogenboom HR, Winter G. (1992) By-passing immunisation. Human antibodies from synthetic repertoires of germline VH gene segments rearranged in vitro. J. Mol. Biol., 227(2): 381-8.

Horton JJ, Holden CA, Ward PJ, MacDonald DM, Sanderson AR. (1985) Exploitation of phylogenetic distance in cell surface immune labeling: studies with beta 2-microglobulin. J. Invest. Dermatol., 84(2): 96-9.

Johnson PM, Faulk WP. (1976) Rheumatoid factor: its nature, specificity, and production in rheumatoid arthritis. Clin. Immunol. Immunopathol., 6(3): 414-30.

Käpyaho K, Tanner P, Weber T. (1989) Effect of complement binding on a solid-phase immunometric TSH assay. Scand. J. Clin. Lab. Invest., 49(3): 211-15.

Kastern W, Holst E, Nielsen E, Sjöbring U, Björck L. (1990) Protein L, a bacterial immunoglobulin-binding protein and possible virulence determinant. Infect. Immu., 58(5): 1217-22.

Kelly CP, Chetham S, Keates S, Bostwick EF, Roush AM, Castagliuolo I, LaMont JT, Pothoulakis C. (1997) Survival of anti-Clostridium difficile bovine immunoglobulin concentrate in the human gastrointestinal tract. Antimicrob. Agents Chemother., 41(2): 236-41.

Knittler MR, Haas IG. (1992) Interaction of BiP with newly synthesized immunoglobulin light chain molecules: cycles of sequential binding and release. EMBO J., 11(4): 1573-81.

Kollberg H, Carlander D, Olesen H, Wejåker PE, Johannesson M, Larsson A. (2003) Oral administration of specific yolk antibodies (IgY) may prevent Pseudomonas aeruginosa infections in patients with cystic fibrosis: a phase I feasibility study. Pediatr. Pulmonol., 35(6): 433-40.

Kricka LJ. (1999) Human anti-animal antibody interferences in immunological assays. Clin. Chem., 45(7): 942-56.

Krüger C, Pearson Sk, Kodama Y, Vacca Smith A, Bowen WH, Hammarström L. (2004) The effects of egg-derived antibodies to glucosyltransferases on dental caries in rats. Caries Res., 38(1): 9-14.

Lang IM, Barbas CF 3rf, Schleef RR. (1996) Recombinant rabbit Fab with binding activity to type-1 plasminogen activator inhibitor derived from a phage-display library against human alpha-granules. Gene, 172(2): 295-8.

Larsson A, Lindahl TL. Chicken antibodies: a tool to avoid interference, in immunological assays, Avian Immunology in Progress. Tours (France), Ed. INRA, Aug. 31-Sep. 2, 1993 (Les Colloques, n 62, pp. 97-102).

Larsson A, Mellstedt H. (1992) Chicken antibodies: a tool to avoid interference by human anti-mouse antibodies in ELISA after in vivo treatment with murine monoclonal antibodies. Hybridoma, 11(1): 33-9.

Larsson A, Sjöquist J. (1989) Binding of complement components C1q, C3, C4 and C5 to a model immune complex in ELISA. J. Immunol. Methods, 119(1): 103-9.

Larsson A, Wejåker PE, Forsberg PO, Lindahl T. (1992) Chicken antibodies: a tool to avoid interference by complement activation in ELISA. J. Immunol. Methods, 156(1): 79-83.

Leslie GA, Clem LW. (1969) Phylogen of immunoglobulin structure and function. 3. Immunoglobulins of the chicken. J. Exp. Med., 130(6): 1337-52.

Lindahl TL, Festin R, Larsson A. (1992) Studies of fibrinogen binding to platelets by flow cytometry: an improved method for studies of platelet activation. Thromb. Haemost., 68(2): 221-5.

Losonsky GA, Johnson JP, Winkelstein JA, Yolken RH. (1985) Oral administratino of human serum immunoglobulin in immunodeficient patients with viral gastroenteritis. A pharmacokinetic and functional analysis. J. Clin. Invest., 76(6): 2362-7.

Malhotra R, Wormald MR, Rudd PM, Fischer PB, Dwek RA, Sim RB. (1995) Glycosylation changes of IgG associated with rheumatoid arthritis can activate complement via the mannose-binding protein. Nat. Med.; 1(3): 237-43.

Marks JD, Hoogenboom HR, Bonnert TP, McCafferty J, Griffiths AD, Winter G. (1991) By-passing immunization. Human antibodies from V-gene libraries displayed on phage. J. Mol. Biol., 222(3): 581-97.

Matsuda H, Mitsuda H, Nakamura N, Furusawa S, Mohri S, Kitamoto T. (1999) A chicken monoclonal antibody with specificity for the N-terminal of human prion protein. FEMS Immunol. Med. Microbiol., 23(3): 189-94.

Miller GW, Nussenzweig V. (1975) A new complement function: solubilization of antigen-antibody aggregates. Proc. Natl. Acad. Sci. USA, 72(2): 418-22.

Mine Y, Kovacs-Nolan J. (2002) Chicken egg yolk antibodies as therapeutics in enteric infectious disease: a review. J. Med. Food, 5(3): 159-69.

Nakamura N, Shimokawa M, Miyamoto K, Hojyo S, Horiuchi H, Furusawa S, Matsuda H. (2003) Two expression vectors for the phage-displayed chicken monoclonal antibody. J. Immunol. Methods, 280(1-2): 157-64.

Nishinaka S, Matsuda H, Murata M. (1989) Establishment of a chicken X chicken hybridoma secreting specific antibody. Int. Arch. Allergy Appl. Immunol., 89(4): 416-9.

Nishinaka S, Suzuki T, Matsuda H, Murata M. (1991) A new cell line for the production of chicken monoclonal antibody by hybridoma technology. J. Immunol. Methods, 139(2): 217-22.

Nishinaka S, Akiba H, Nakamura M, Suzuki K, Suzuki T, Tsubokura K, Horiuchi H, Furusawa S, Matsuda H. (1996) Two chicken B cell lines resistant to ouabain for the production of chicken monoclonal antibodies. J. Vet. Med. Sci., 58(11): 1053-56.

Nissim A, Hoogenboom HR, Tomlinson IM, Flynn G, Midgley C, Lane D, Winter G. (1994) Antibody fragments from a 'single pot' phage display library as immunochemical reagents. EMBO J., 13(3): 692-8.

Otani H, Matsumoto K, Saeki A, Hosono A, Comparative Studies on Properties of Hen Egg Yolg IgY and Rabbit Serum IgG Antibodies. Lebensm.-Wiss. U. Technol., 24: 152-158 (1991).

Olovsson M, Larsson A. (1993), Biotin Labelling of Chicken Antibodies and their subsequent use in ELISA and immunohistochemistry. Comp. Immun. Microbiol. Infect. Dis., 16(2): 145-152.

Parvari R, Ziv E, Lantner F, Heller D, Schechter I. (1990) Somatic diversification of chicken immunoglobulin light chains by point mutations. Proc. Natl. Acad. Sci. USA, 87(8):3072-76.

Parvari R, Avivi A, Lentner F, Ziv E, Tel-Or S, Burstein Y, Schechter I. (1988) Chicken immunoglobulin gamma-heavy chains: limited VH gene repertoire, combinatorial diversification by D gene segments and evolution of the heavy chain locus. EMBO J., 7(3): 739-44.

Ramirez AD, Rocha EM, Krettli AU. (1995) Antisporozoite antibodies with protective and nonprotective activities: in vitro and in vivo correlations using Plasmodium gallinaceum, an avian model. J. Eukaryot. Microbiol., 42(6): 705-8.

Reilly RM, Domingo R, Sandhu J. (1997) Oral delivery of antibodies. Future pharmacokinetic trends. Clin. Pharmacokinet., 32(4): 313-23.

Roos A, Bouwman LH, van Gijlswijk-Janssen DJ, Faber-Krol MC, Stahl GL, Daha MR. (2001) Human IgA activates the complement system via the mannan-binding lectin pathway. J. Immunol., 167(5): 2861-68.

Rubinstein E, Kouns WC, Jennings LK, Boucheix C, Carroll RC. (1991) Interaction of two GPIIb/IIIa monoclonal antibodies with platelet Fc receptor Fc receptor (Fc gamma RII). Br. J. Haematol., 78(1): 80-6.

Sambrook J, Fritsch EF, Maniatis T. Molecular Cloning. A Laboratory Manual ($2^{nd}$ Ed., Cold spring Harbor Press, 1989.).

Sapats SI, Heine HG, Trinidad L, Gould GJ, Foord AJ, Doolan SG, Prowse S, Ignjatovic J. (2003) Generation of chicken single chain antibody variable fragments (scFv) that differentiate and neutralize infectious bursal disease virus (IBDV). Arch. Virol., 148(3): 497-515.

Shimizu M, Nagashima H, Sano K, Hashimoto K, Ozeki M, Tsuda K, Hatta H. (1992) Molecular stability of chicken and rabbit immunoglobulin G. Biosci. Biotechnol. Biochem., 56(2): 270-4.

Smith DJ, King WF, Godiska R. (2001) Passive transfer of immunoglobulin Y antibody to *Streptococcus* mutans glucan binding protein B can confer protection against experimental dental caries. Infect. Immun., 69(5): 3135-42.

Song CS, Yu JH, Bai DH, Hester PY, Kim KH. (1985) Antibodies to the alpha-subunit of insulin receptor from eggs of immunized hens. J. Immunol., 135(5): 3354-59.

Sun S, Mo W, Ji Y, Liu S. (2001) Preparation and mass spectrometric study of egg yolk antibody (UgY) against rabies virus. Rapid Commun. Mass Spectrom., 15(9): 708-12.

Suzuki N, Lee YC. (2004) Site-specific N-glycosylation of chicken serum IgG. Glycobiology, 14(3): 275-92.

Suzuki N, Khoo KH, Chen CM, Chen HC, Lee YC. (2003) N-glycan structures of pigeon IgG: a major serum glycoprotein containing Gal-alpha1-4 Gal termini. J. Biol. Chem., 278(47): 46293-306.

Takahashi N, Nakagawa H, Fujikawa K, Kawamura Y, Tomoya N. (1995) Three-dimensional elution mapping of pyridlaminated N-linked neutral and sialyl oligosaccharides. Anal. Biochem., 226(1): 139-46.

van de Winkel JG, Capel PJ. (1993) Human IgG Fc receptor heterogeneity: molecular aspects and clinical implications. Immunol. Today, 14(5): 215-21.

van de Wetering JK, van Golde LM, Batenburg JJ. (2004) Collectins: players of the innate immune system. Eur. J. Biochem., 271(7):1229-49.

van Dijk MA, van de Winkel JG. (2001) Human antibodies as next generation therapeutics: Curr. Opin. Chem. Biol., 5(4): 368-74.

Wan T, Beavil RL, Fabiane SM, Beavil AJ, Sohi MK, Keown M, Young RJ, Henry AJ, Owens RJ, Goulf HJ, Sutton BJ. (2001) The crystal structure of IgE Fc reveals an sysmmetrically bent conformation. Nat. Immunol., 3(7): 681-6.

Warr GW, Magor KE, Higgins DA. (1995) IgY: clues to the origins of modern antibodies. Immunol. Today, 16(8): 392-8.

Whaley K, Methods in Complement for Clinical Immunologists (Elsevier Health Sciences, publisher), pp. 77-139 (1985).

Yamanaka HI, Inoue T, Ikeda-Tanaka O. (1996) Chicken monoclonal antibody isolated by a phage display system. J. Immunol., 157(3): 1156-62.

\* cited by examiner scFv-C$_H$1-4 IgY
(III)

scFv-C$_H$2-4 IgY
(IV)

scFv-C$_H$1-2 IgY
(V)

scFv-C$_H$2 IgY
(VI)

IgY
(VII)

IgYΔFc
(VIII)

IgEY
(XIII)

Fig. 7
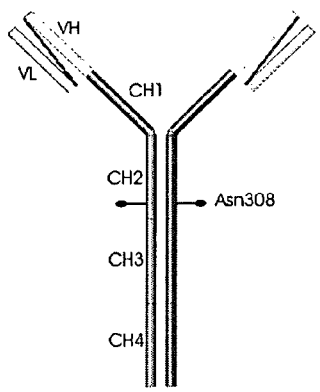
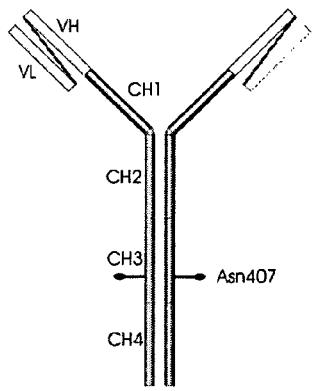
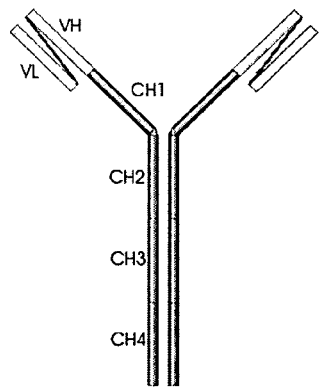
scFv-C$_H$1-4 IgYN407Q (XVIII)    scFv-C$_H$1-4 IgYN308Q (XIX)    scFv-C$_H$1-4 IgYN407,308Q (XX)
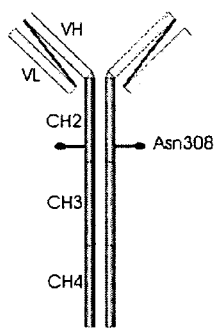
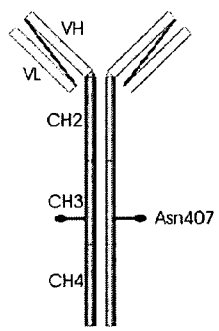
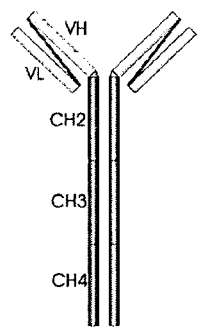
scFv-C$_H$2-4 IgYN407Q (XXI)    scFv-C$_H$2-4 IgYN308Q (XXII)    scFv-C$_H$2-4 IgYN407,308Q (XXIII)
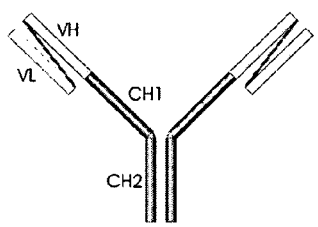
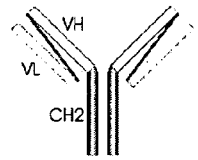
scFv-C$_H$1-2 IgYN308Q (XXIV)    scFv-C$_H$2 IgYN308Q (XXV)

Fig. 8 avian lambda light chain constant region coding region cagcccaagg tggcccccac catcaccctc
ttcccaccgt caaaggagga gctgaacgaa gccaccaagg ccaccctggt gtgcctgata
aacgacttct accccagccc agtgactgtg gattgggtga tcgatggctc cacccgctct
ggcgagacca cagcaccaca gcggcagagc aacagccagt atatggccag cagctatctg
tcactgtctg ccagcgactg gtcaagccac gagacctaca cctgcagggt cacacacgac
ggcacctcta tcacgaagac cctgaagagg tccgagtgct aa upsilon heavy chain constant region coding region cgcgagc
cccacatcgc cccccgatt gtaccctcta tccgcctgtt gttccgactc ggctgtcccg
ccggccgtgg gctgcctgtt gtccccttcg tccgccggcg gcatctcctg ggagggctcc
ggaggtacgg cggtggccgg cagagtttcg gggaccccg tgaagctcag cttcgtccgc
ctcagccccg gcgagaagag gaaaagcttc gtctgcagcg ccgcccccgg ggggcgctg
ctcaaaaagg aggtgcaggt ctgccgggta gatcccgtac cgcctgtagc cccagaggtg
caggtcctcc acccctcctc ctgcaccccg agccaatccg agtcggtgga gctgttgtgt
ttggtgacgg ggttctcccc ggcgtcggcg gaggtcgaat ggttggtgga cggagtgggg
ggacttttgg tggcctccca aagcccggcg gtccgcagcg gatccaccta cagcctgagc
agccgcgtca acgtcagcgg caccgattgg agggaaggga gagttacag ctgtagggtg
aggcaccccg caaccaacac cgtggtggag gatcacgtca agggatgccc ggacggcgct
cagagctgca gccccatcca gctgtacgcc atcccaccca gcccgggcga gctgtacatc
agcttagacg ccaaactgag gtgcctggtg gtcaacctgc ccagcgattc cagcctcagc
gtcacctgga ccagggagaa gagtgggaac ctccggcccg acccgatggt cctccaagaa
cacttcaacg gcacctacag cgccagcagc gccgtccccg tcagcaccca ggattggtta
tccggggaga ggttcacctg caccgtgcag cacgaggagc tgccctgcc gctcagcaag
agcgtctaca ggaacacggg acccaccacc ccacctctga tctacccctt cgcccccac
ccggaagagc tgtccctctc ccgcgtcacc ctgagctgcc tggtccgcgg cttccgccca
cgtgacatcg agatccggtg gctccgcgac caccgcgccg ttcccgccac cgaattcgtc
accaccgccg tcctcccgga agagagaacc gcaaacggcg ccggcggtga cggcgacacc
ttcttcgtgt acagtaagat gagcgtggag accgccaagt ggaacggcgg gacggtgttc
gcctgcatgg cggtgcacga ggcgctgccc atgcgcttca gccagcgcac gctgcagaaa
caggctggta aataa

Fig. 9

```
Human IgG    VSSASTKGPSVFPLAPSSKSTSGGTAALGCLVKDYFPEPVTVSWNSGALTSGVHTFPAVL 60
Chicken IgY  -SPTSP--PRLYPLSACCSDSAV-PPAVGCLLSPSSAG--GISWEG-SGGTAVAGRVS-- 51
             *.:*.   *  ::**:.....::  ..*:***:.  .   :**:. :  :.*     :

Human IgG    QSSGLYSLSSVVTVPSSSLGTQTYICNVNHKPSNTKVDKKVEPKSCDKTHTCPPCPAPEL 120
Chicken IgY  ---GTPVKLSFVRLSPGEK-RKSFVCSAAPGG--ALLKKEV--QVCRVDPVPPVAPEVQV 103
                *    *.* :....   ::::*..      : :.*:*  : *    . * .*  ::
```

Fig. 10
A: heterotetrameric IgY
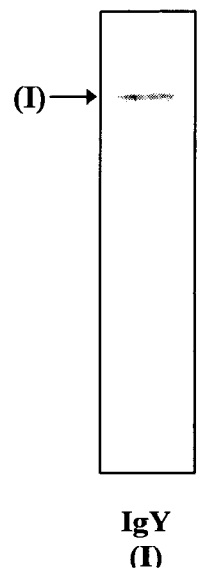
IgY
(I)
B: homodimeric IgY
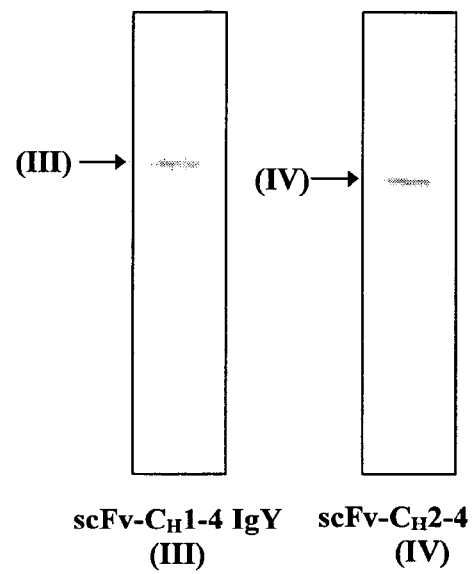
scFv-C$_H$1-4 IgY   scFv-C$_H$2-4 IgY
(III)               (IV)

Fig. 11
A: heterotetrameric chimeric IgY
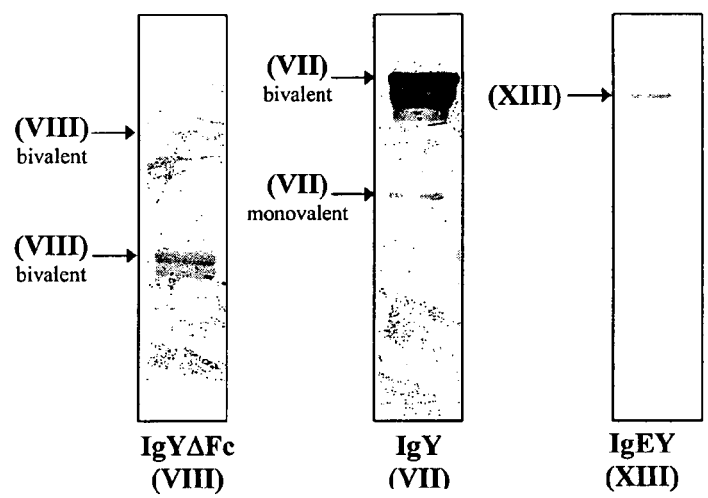
B: homodimeric chimeric IgY
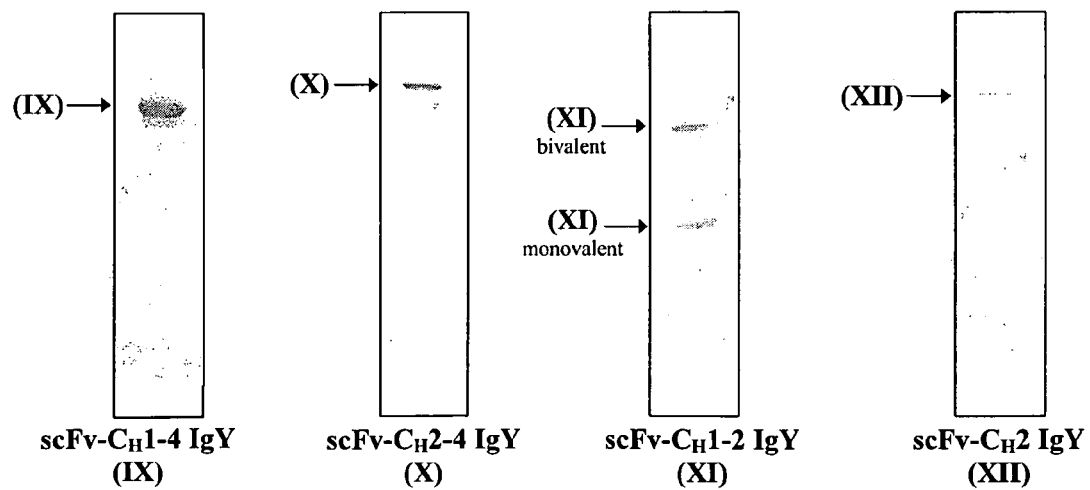

Fig. 14

(I)  (III)  (IV)  Control  Control
            Anti-IBDV mAB  Without antibody

Fig. 15
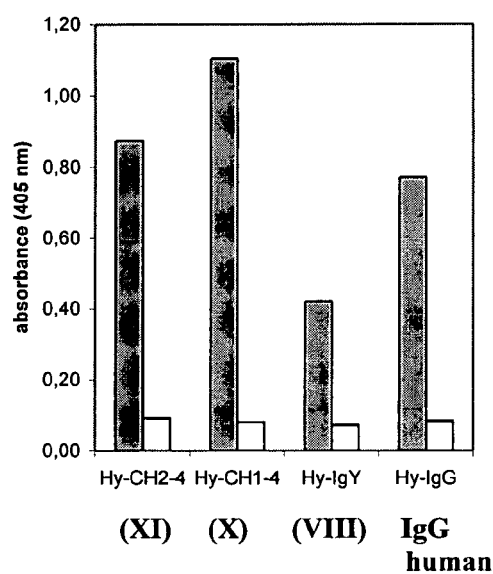
A.
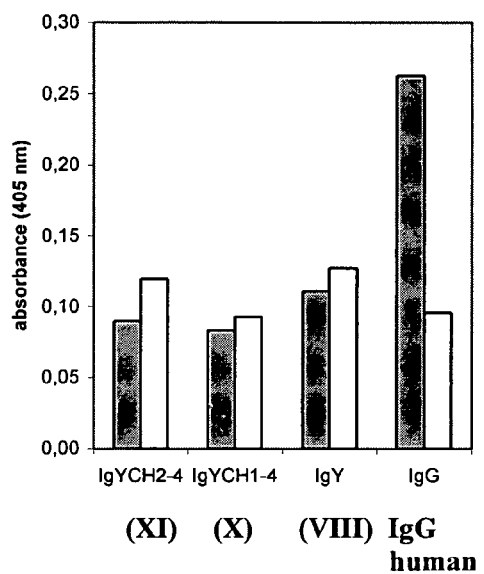
B.

BIVALENT IGY ANTIBODY CONSTRUCTS FOR DIAGNOSTIC AND THERAPEUTIC APPLICATIONS

This application claims priority to European Patent Application No. EPO 05018607.1, filed on Aug. 25, 2005, which is herein incorporated by reference in its entirety.

BACKGROUND

Antibodies play an important role in clinical applications as well as diagnostic assays. Administration of antibodies specific to host pathogens is an attractive approach to establish protective immunity, employed in passive vaccination or in therapy. Antibodies are often used as vehicles that direct a linked moiety, e.g., an active agent or a toxin, to specific sites in the body, where the antigens recognized by the antibodies are expressed. Labelled antibodies can be used for in vivo diagnostics.

The most common application however is the in vitro diagnostic use of antibodies in immunological assays to identify and/or quantify antigens of interest. The most important formats of immunological tests are ELISA (Enyzme linked immunosorbent assay), RIA (Radioimmunosorbent assay) or ELISPOT (Enzyme linked immunospot), as well as flow cytometric tests such as FACS(Fluorescence activated cell sorting) or blots, e.g., Western blot or dot blot. Antibodies are also used in microscopic applications, such as histology, immunofluorescence or electron microscopy. Antibodies are also used in biotechnological applications, e.g., for purification of the respective antigens.

Typically, antibodies of the Immunoglobulin G (IgG) isotype are used is these applications, although antibodies of other isotypes, e.g., Immunoglobulin M (IgM), are also employed. Polyclonal antibodies are normally generated by immunization of animals, such as mice, rats, rabbits etc., and isolation of antibodies from the serum, following standard protocols. Generation of monoclonal antibodies, which only have a single antigenic specificity, by fusion of antibody-producing lymphocytes from immunized animals with myeloma cells is also well established.

However, use of such antibodies in practice also raises a number of difficulties.

Rheumatoid factor (RF) and human anti-mouse IgG antibodies (HAMA) are probably the most well known causes of false positive or false negative reactions in immunological assays (Boscato L M, Stuart M C, Clin Chem 34, 27-33, 1988). RF is an auto-antibody that reacts with the Fc part of IgG. The disease most often associated with RF is rheumatoid arthritis, but RF can be found in serum from patients with many other diseases and also in 3-5% of healthy blood donors (Johnson P M, Faulk W P, Clin Immunol Immunopathol 6, 414-430, 1976). Production of HAMA is mainly the result of therapeutic approaches with mouse monoclonal antibodies, but HAMA may also be found in serum from patients who have not been treated with antibodies. RF or HAMA may react with both the capture antibody and the detection antibody in a sandwich assay, thereby mimicking antigen activity. A reaction with the detection antibody results in formation of an immune complex which may influence the activity of the detection antibody. HAMA may also react with the antigen-binding region of the detection antibody, thereby impairing or inhibiting antigen binding. The problem of RF and HAMA interference will increase as the sensitivity of the assay increases. Interference by anti-IgG antibodies and antibody-binding substances have been demonstrated in approximately 40% of serum samples from healthy individuals in an immunoradiometric assay (Boscato L, Stuart M, Clin Chem 32, 1491-1495, 1986). RF and HAMA will also give erroneous results in nephelometry and turbidimetry as they change the size of antigen-antibody complex (Chambers R E, et al., Ann Clin Biochem 24, 520-524, 1987).

The prevalence of human anti-mammalian antibodies causing potential interferences in immunological assays varies from 1-80% in the general population (Kricka L J, Clin. Chem. 45, 942-956, 1999).

Furthermore, the IgG antibodies normally used for clinical assays, bound to a solid phase, and antigen-antibody complexes comprising such antibodies, as well as IgM antibodies, can activate the human complement system (Larsson A, Sjoquist J, J Immunol Methods 119, 103-109, 1989). Activated C4 molecules bind to the Fab region of IgG and may interfere with the antigen binding (Campbell R D, et al., Biochem J 189, 6780, 1980). Complement components may also solubilize precipitated immune complexes and prevent soluble immune complexes from precipitating (Baatrup G, et al., Scand J Immunol 23, 397-406, 1986; Miller G W, Nussenzweig V, Proc Natl Acad Sci USA 72, 418-422, 1975).

In clinical laboratories, most analyses are performed on serum samples. A newly obtained serum sample contains active complement, but the activity declines during storage and handling (Whaley, K. Methods in complement for clinical immunologists, Churchill Livingstone, 1985). Accordingly, the complement activity may vary between different patients and also between different samples from the same patient. To avoid activation of the complement cascade, EDTA is often included in tubes used for blood sampling. EDTA prevents complement activation and coagulation by sequestering calcium ions. Most of the standards and controls used have been stored and contain an inactive complement system. This difference in activity between the samples and the standards will cause erroneous results. Complement activation was shown to interfere in an immunometric TSH assay and depressed the TSH values by up to 40% (Kapyaho K, et al., Scand J Clin Lab Invest 49, 211215, 1989).

An additional problem in working with cells or tissue—or with in vivo applications—is the presence of receptors for immunoglobulins. Human FcγRI has a high affinity for monomeric IgG, while FcγRII and FcγRIII mainly bind IgG complexes. There is often some aggregated IgG formed during the purification of IgG or during the labeling procedures that will increase the binding to FcγRII and FcγRIII receptors. Interaction with Fc receptors may cause an increased background staining in immunological tissue analysis. When working with living cells, the interaction with Fc receptors may cause cell activation and changes in the expression of surface proteins. For example, it has been shown that IgG antibodies used in flow cytometry form immune complexes that cause platelet activation and changes in the expression of the GpIIb-IIIa receptor (Lindahl T L, et al., Thromb Haemost 68, 221-225, 1992; Rubinstein E, et al., Br J Haematol 78, 80-86, 1991). Immune complexes containing IgG may also stimulate the production of cytokines (van de Winkel J G, Capel P J, Immunol Today 14, 215-221, 1993).

Similarly, Staphylococcal protein A and Streptococcal protein G are Fc-binding bacterial proteins which are widely used for their ability to bind to IgG. Bacteria of the *Staphylococcus aureus* Cowan 1 strain and group C *Streptococcus* sp. are used as immunoadsorbent for IgG. Staphylococci and Streptococci are often found in bacterial samples. When present, they may bind detection antibodies with specificities for other bacteria and cause erroneous results. There are also other bacteria (e.g. *Peptostreptococcus magnus, Streptococcus suis* and *Actinobacillus actinomycetemcomitans*) with Ig-binding capabilities (Engstrom P E, et al., J Clin Periodontol 20, 746-751, 1993; Benkirane R, et al., FEMS Immunol Med Microbial 20, 121-127, 1998; Kastern W, et al., Infect Immun 58, 1217-1222, 1990).

One approach to avoid the above mentioned problems, e.g. of cross-reactivity and complement activation, is the use of antibody fragments instead of complete antibodies. For example, IgG antibodies can be enzymatically cut by papain into two Fab fragments (fragment antigen binding) and one Fc fragment (fragment cristallizable). IgG antibodies contain two light and two heavy chains. The light chains have a molecular mass of about 25 kDa and the heavy chains of about 50 kDa. The heavy chain has one variable (V) region and three constant (C) regions. The light chain is composed of one variable and one constant domain. IgG is bivalent, i.e. it has two antigen binding sites. These are composed of the variable domains of both heavy and light chains. The hinge region between the two "arms" of the antibody and the "stem" region gives flexibility to the molecule. Fab fragments thus carry one antigen binding site (they are monovalent).

Recombinant production of Fab fragments is possible. In a preferred form, light and heavy chain domains are formed by a single peptide chain, which can be recombinantly generated (scFv, single chain fragment variable). Libraries of scFv, in particular as phage display libraries, are available in the art, which facilitate generation of recombinant antibodies or scFv specific for a given antigen.

One major limitation of scFv or Fab molecules, however, is their monovalent format, impairing the affinity of these molecules and, thereby, their applicability for therapeutic and diagnostic applications. Utilizing short linker sequences for the construction of scFv, formation of scFv dimers can be favored (Holliger P, et al., Pro. Natl Acad Sci USA 90, 6444, 1993). However, such dimers ('diabodies') are formed by noncovalent association and may dissociate. Alternatively, bivalent $Fab_2$ fragments can be used, which still contain the hinge region, wherein the two heavy chains are connected by a disulfide linkage. $Fab_2$ can be produced by enzymatic digestion of antibodies with pepsin.

However, especially for diagnostic applications, another major limitation of scFv, Fab and $Fab_2$ molecules is the lacking Fc region. As a result, many of the advantages offered by antibodies for immunological detection procedures, such as recognition by secondary antibodies to the Fc region, cannot be realized.

The person skilled in the art is therefore faced with the need of generating improved antibodies that avoid or minimize the above mentioned problems in the use of complete IgG antibodies, e.g. of cross-reactivity and complement activation that can lead to false-positive and -negative results in diagnostic assays, but further do not show the disadvantages brought about by use of scFv, Fab and $Fab_2$ molecules.

SUMMARY OF THE INVENTION

This problem is solved by the subject matter of the claims. In particular, the present invention provides a chimeric bivalent homodimeric or heterotetrameric antibody construct comprising at least one IgY constant domain selected from the group consisting of $C_H2$, $C_H3$, or $C_H4$.

These constructs comprise recombinant, covalently stabilized bivalent IgY antibodies and truncated bivalent IgY antibody constructs, the format of all of which can be homodimeric or heterotetrameric. In particular, the present invention relates to bivalent chimeric antibody constructs comprising IgY constant domains and mammalian variable regions, bivalent chimeric antibody constructs comprising a combination of mammalian and IgY constant domains and mammalian variable regions, as well as truncated formats of bivalent avian chimeric IgY antibodies lacking either IgY constant domains $C_H3$ and $C_H4$ or only the $C_H4$ IgY domain. The chimeric constructs allow to combine the advantageous properties of IgY constant domains with the antigen binding characteristics of well established mammalian monoclonal antibodies. Since the development of monoclonal antibodies with optimal antigen binding characteristics is extremely time- and money-consuming, utilization of the variable domain of existing valuable antibodies provides many advantages. The approach is useful for both diagnostic and therapeutic applications.

It is still another object of the present invention to provide monoclonal antibodies and fragments thereof with IgY properties that are more stable under acidic conditions than natural IgY molecules. Such antibodies are chimeric constructs consisting of constant domains of the IgY heavy chain and mammalian immunoglobulin domains that were found to be responsible for the higher molecular stability of mammalian immunoglobulins under acidic conditions. Preferred constructs comprise VL (variable light chain) and CL (constant light chain) domains of mammalian origin which in contrast to IgY light chains are stabilized by an additional intra-chain disulfide linkage between the VL and CL domains. Other preferred constructs also comprise VH (variable heavy chain) and CH1 (constant heavy chain domain 1) domains of mammalian origin. Thereby, the content of stabilizing β-structures is increased, since mammalian constant domains contain more β-sheets than those of IgY. Further preferred constructs comprise mammalian hinge regions to provide an improved resistance to denaturing agents.

Additionally, the present invention provides non-gylcosylated recombinant monoclonal IgY antibodies, fragments thereof, non-glycosylated recombinant IgY antibody constructs, and non-glycosylated chimeric IgY antibody constructs, all of which are capable of bivalent antigen binding due to their covalently stabilized dimeric form. The absence of N-glycans on all of these antibodies and antibody constructs guarantees a lack of interference by C-type lectins in diagnostic and therapeutic applications. Compared to glycosylated IgY antibodies, non-glycosylated bivalent recombinant IgY antibodies and related constructs provide a higher degree of reliability in diagnostic assay procedures and a higher therapeutic efficacy when orally administered.

It is still another object of the present invention to provide nucleic acid sequences and vectors encoding the antibody constructs of the invention, as well as mammalian host cells transfected with these sequences.

FIGURE LEGENDS

FIG. 1: Bivalent heterotetrameric antibody molecules comprising constant and variable domains of avian origin.

Figure 2:
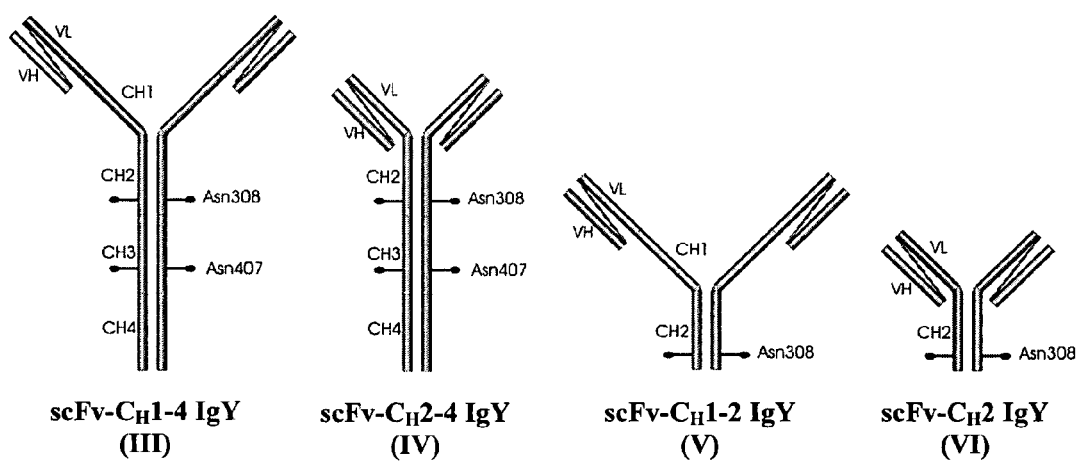

FIG. 2: Bivalent homodimeric antibody molecules comprising constant and variable domains of avian origin.

Figure 3:
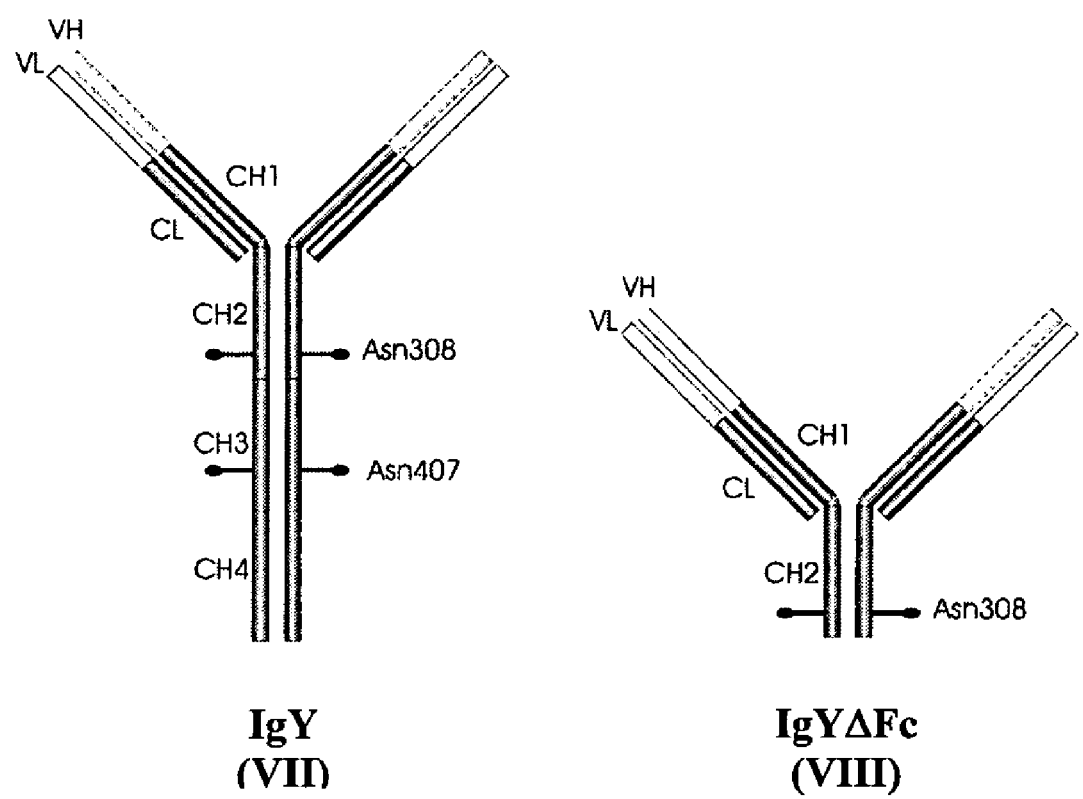

FIG. 3: Bivalent heterotetrameric antibody molecules comprising constant domains of avian origin and variable domains of mammalian origin.

Figure 4:
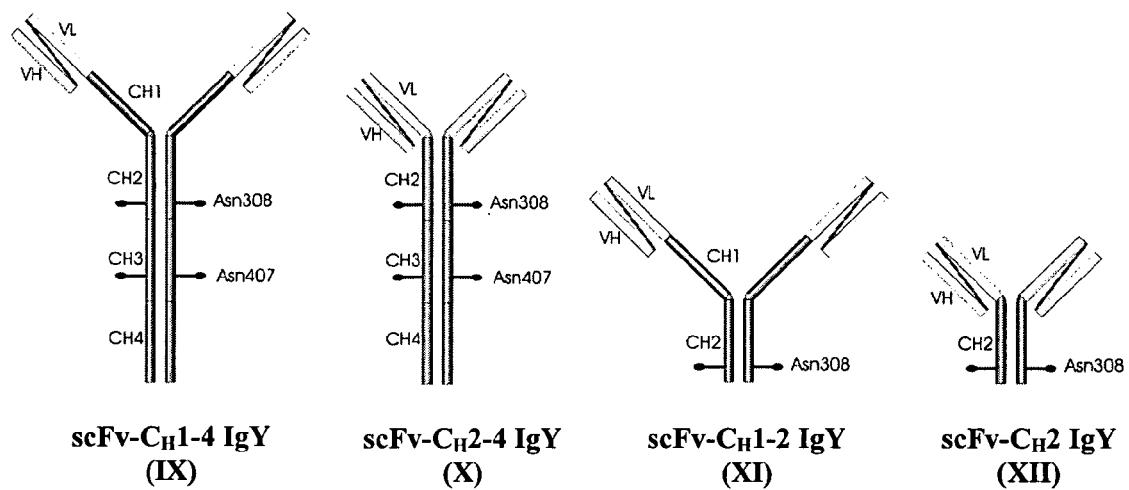

FIG. 4: Bivalent homodimeric antibody molecules comprising constant domains of avian origin and variable domains of mammalian origin.

Figure 5:
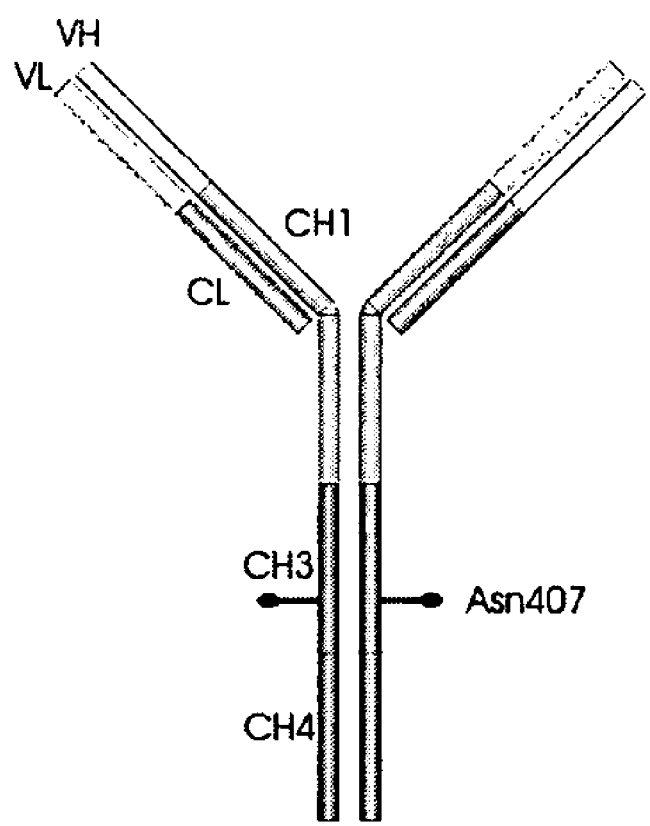

FIG. 5: Bivalent heterotetrameric antibody molecules comprising a combination of mammalian and IgY constant domains and variable domains of mammalian origin (IgE $C_L$, $C_H1$, $C_H2$ domains, IgY $C_H3$, $C_H4$ domains).

Figure 6:
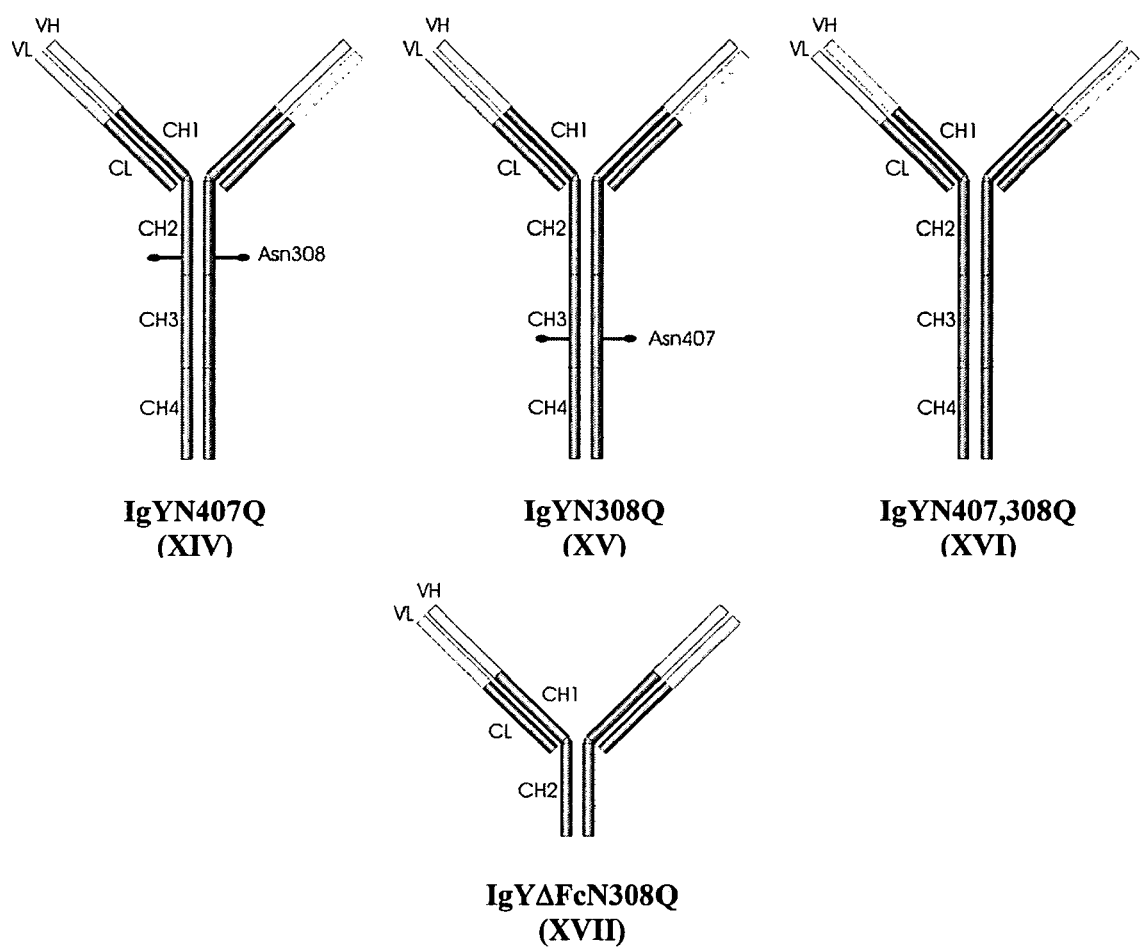

FIG. 6: Mono- and non-glycosylated bivalent heterotetrameric antibody molecules comprising constant domains of avian origin and variable domains of mammalian origin.

FIG. 7: Mono- and non-glycosylated bivalent homodimeric antibody molecules comprising constant domains of avian origin and variable domains of mammalian origin.

FIG. 8: A: chicken IgY lambda light chain constant region coding region: SEQ ID NO:48 B: chicken upsilon heavy chain constant region coding region $C_H1-4$: SEQ ID NO:49 (domains of the heavy chain constant regions are defined according to a conserved domain architecture retrieval tool (Geer et al., 2002).

FIG. 9: Alignment of the $C_H1$ heavy chain constant domains of chicken IgY and human IgG reveals an overall identity of only 20% (IgY $C_H1$ domain: SEQ ID NO:46, IgG $C_H1$ domain: SEQ ID NO:47).

FIG. 10: Western blot analysis of purified recombinant antibodies. After purification by Ni-NTA (NTA: nitrilotriacetic acid) agarose chromatography or affinity chromatography using immobilized antigen, the antibodies were subjected to SDS-PAGE under non-reducing conditions and then analyzed by western blotting. A: heterotetrameric IgY, B: homodimeric IgY construct.

FIG. 11: Western blot analysis of purified recombinant antibodies. After purification by Ni-NTA agarose chromatography or affinity chromatography using immobilized antigen, the antibodies were subjected to SDS-PAGE under non-reducing conditions and then analyzed by western blotting. A: heterotetrameric IgY construct, B: homodimeric IgY construct.

Figure 12:
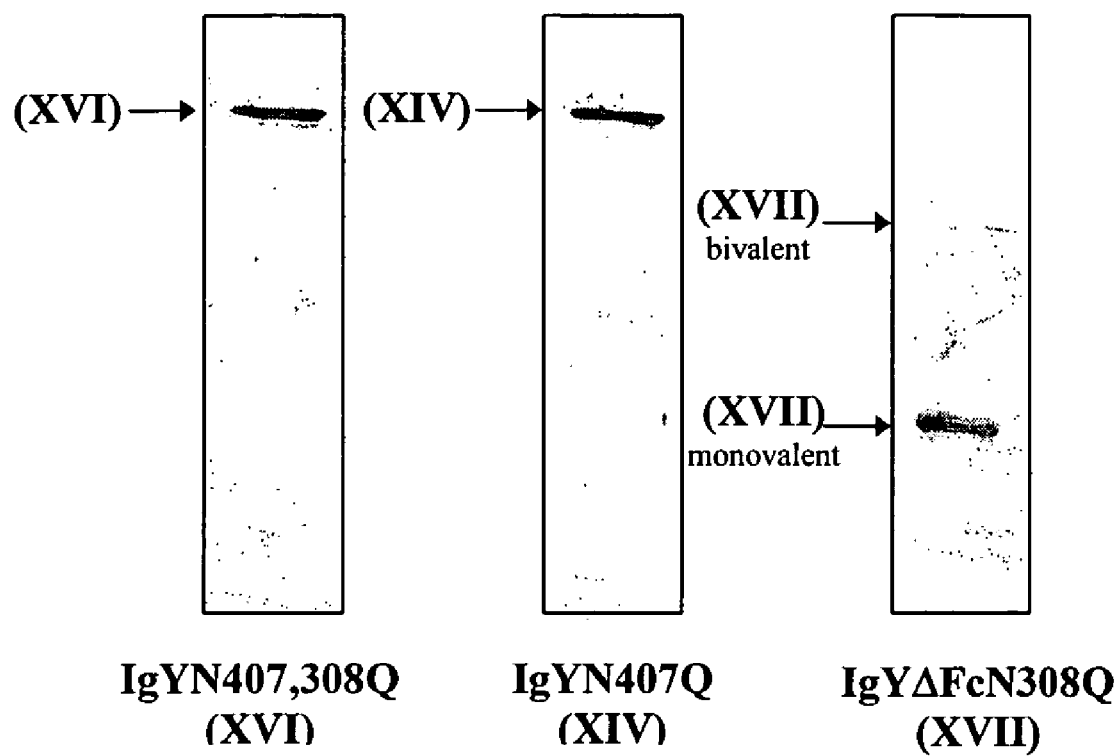

FIG. 12: Western blot analysis of purified recombinant mono- and non-glycosylated bivalent chimeric IgY. After purification by Ni-NTA agarose chromatography or affinity chromatography using immobilized antigen, the antibodies were subjected to SDS-PAGE under non-reducing conditions and then analyzed by western blotting.

Figure 13A:
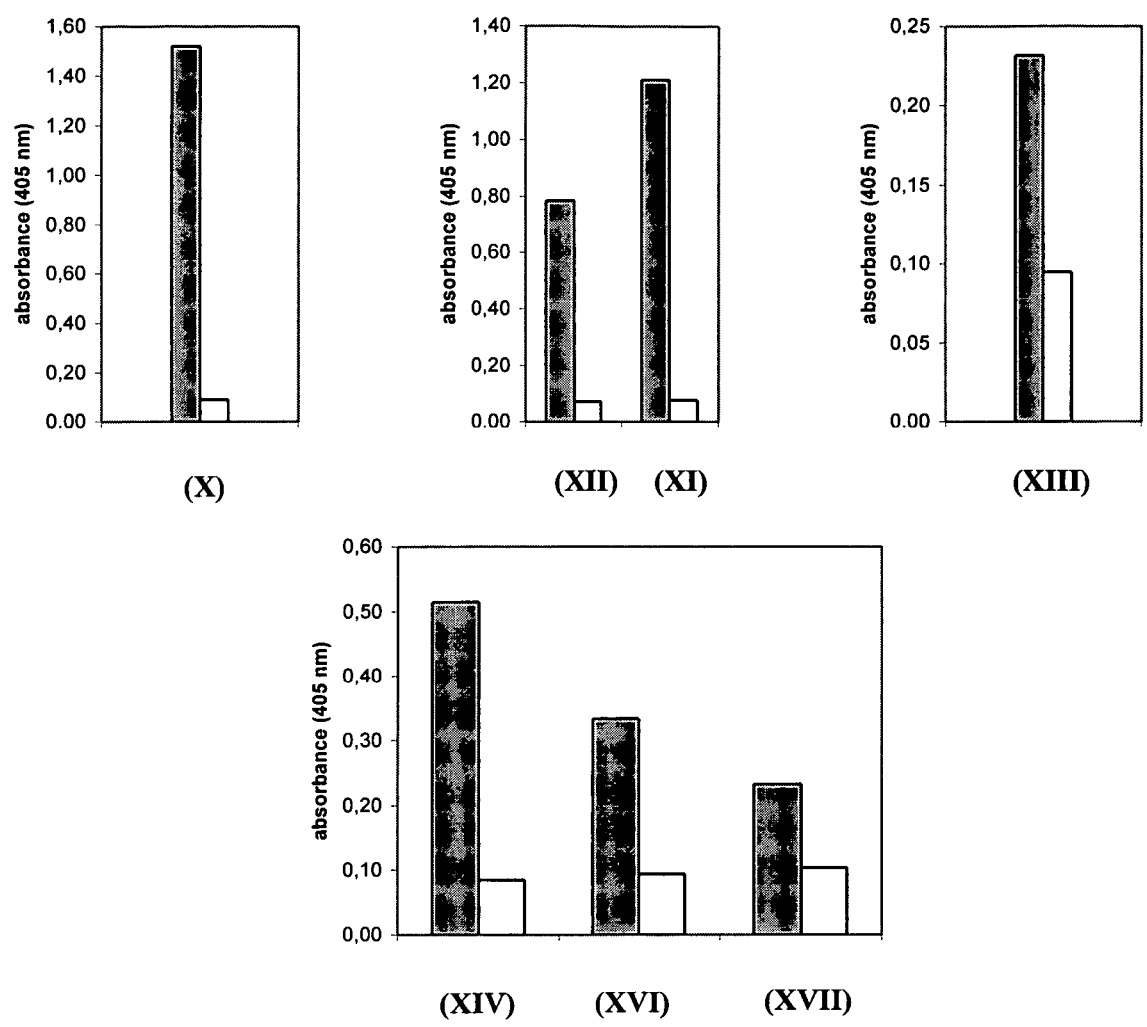

FIG. 13A: Immunoreactivity of recombinant antibodies with specificity for hen egg lysozyme. The immuno-reactivity of IgY antibodies and corresponding scFv-derivatives (filled bars) was analyzed by ELISA (controls by omission of lysozyme: open bars).

Figure 13B:
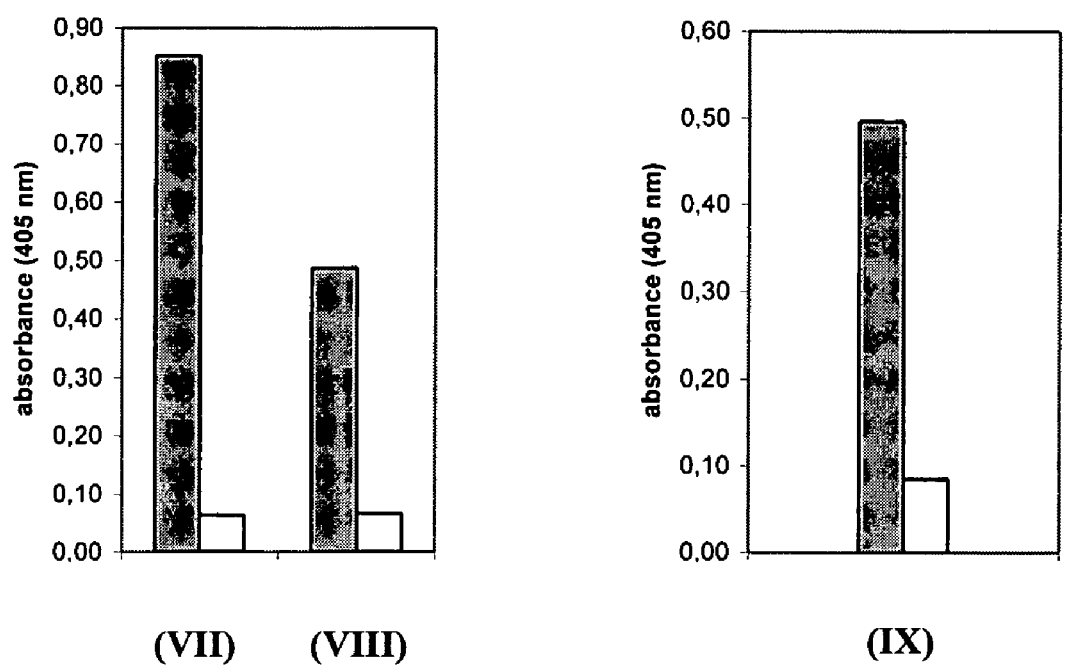

FIG. 13B: Immunoreactivity of recombinant antibodies with specificity for hen egg lysozyme. The immuno-reactivity of IgY antibodies and corresponding scFv-derivatives (filled bars) was analyzed by ELISA (controls by omission of lysozyme: open bars).

FIG. 14: Immunoreactivity of recombinant antibodies with specificity for IBDV (Infectious Bursal Disease Virus). The immunoreactivity was determined by dot blot analysis.

FIG. 15: Reactivity of recombinant IgY antibodies with secondary reagents. A. Detection of IgY constructs was performed with anti-chicken IgY-HRP (Horse-readish peroxidase) conjugate, of human IgG with anti-human IgG-HRP conjugate. B. Detection of both IgY constructs and human IgG was performed with protein A-HRP conjugate.

Figure 16:
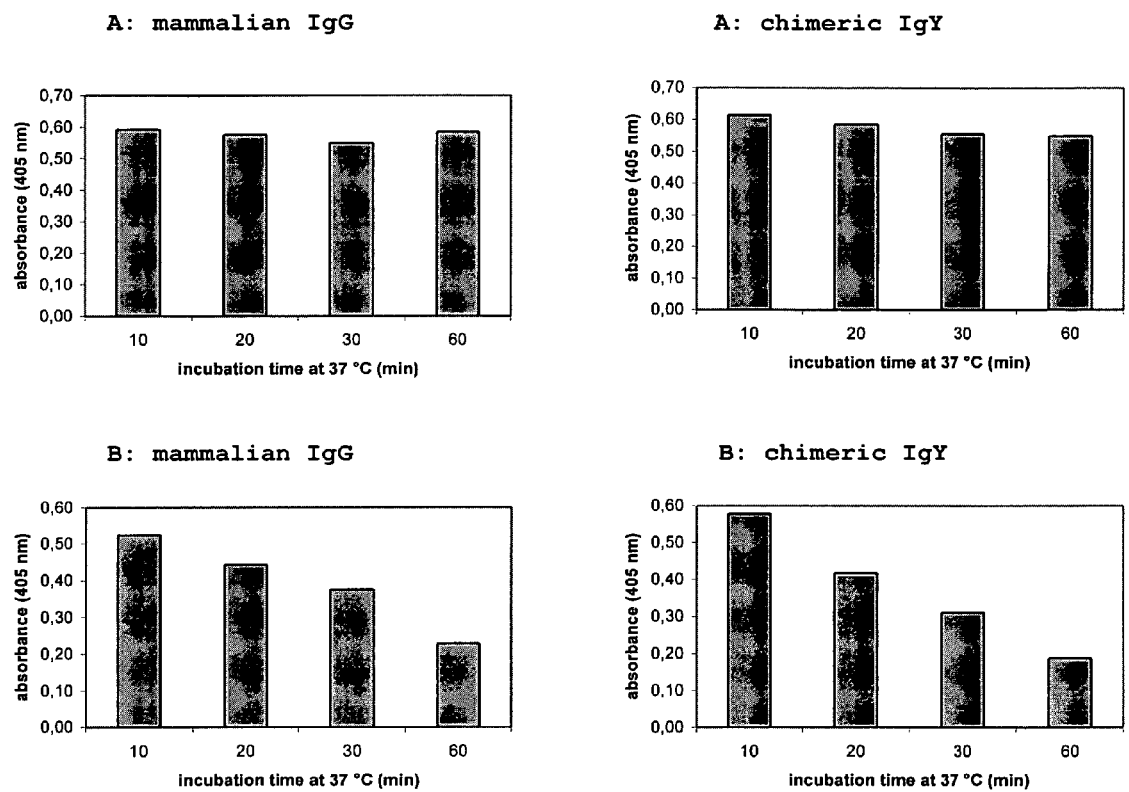

FIG. 16: Immunoreactivity of chimeric IgY (VII) and mammalian IgG, both with specificity for hen egg lysozyme, after incubation under acidic conditions. A: Stability at pH 3.5. B: Stability at pH 3.0.

Figure 17:
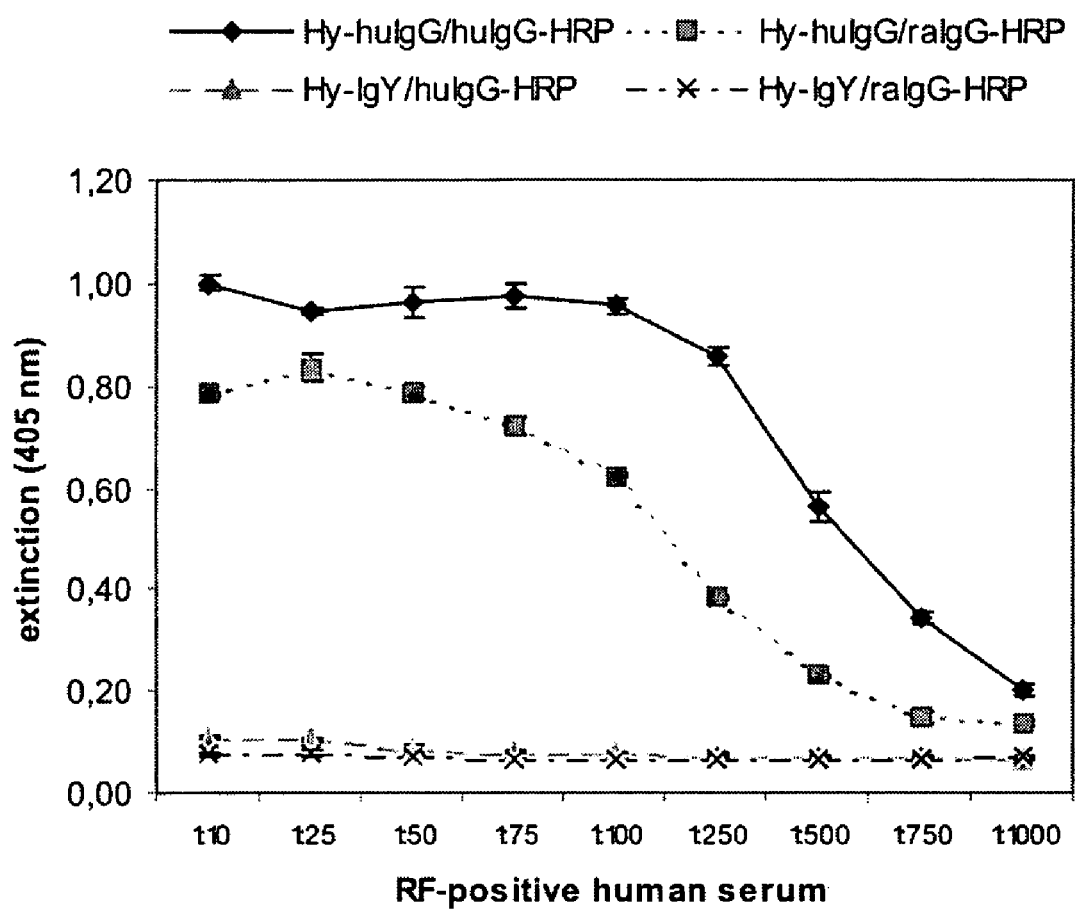

FIG. 17: Lack of interference of chimeric avian monoclonal antibodies with RF-positive human serum. The interference of human chimeric monoclonal antibodies (diamonds and squares) and the lack of interference of chimeric avian monoclonal antibodies (triangles and crosses) were analysed by ELISA.

Figure 18:
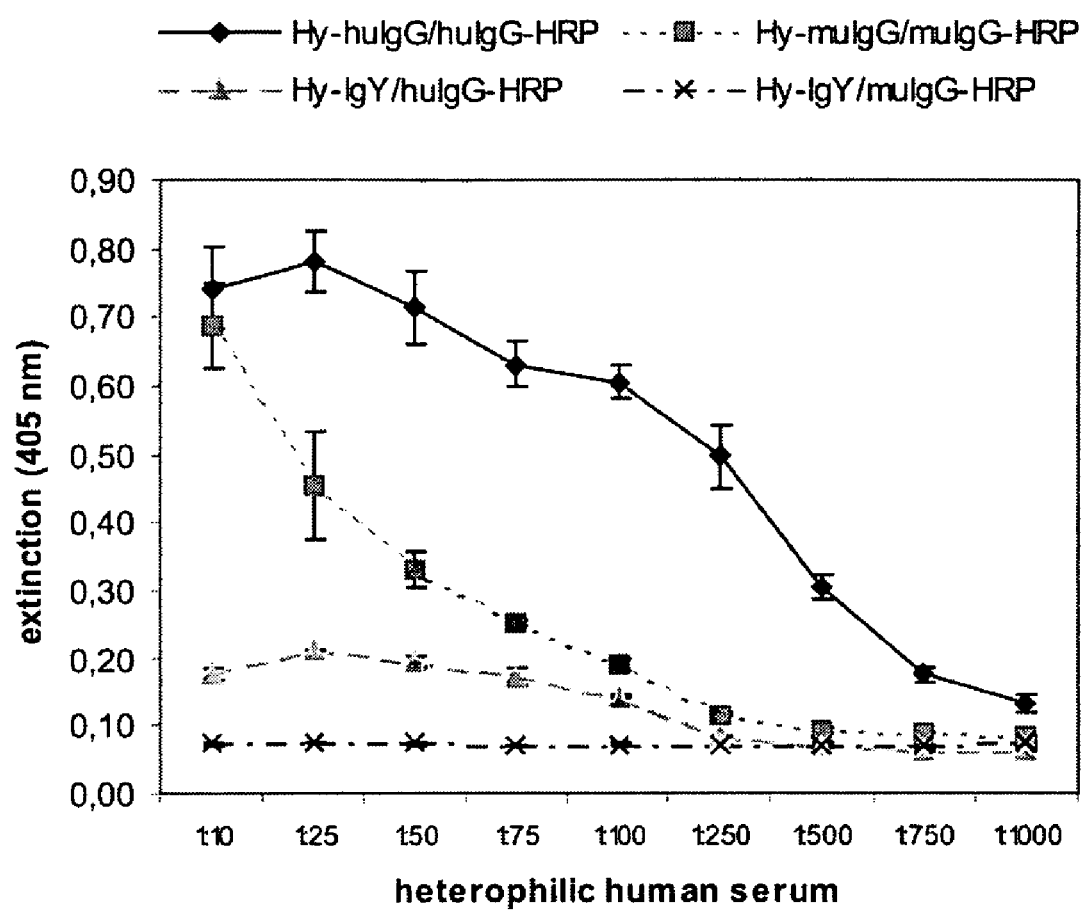

FIG. 18: Lack of interference of chimeric avian monoclonal antibodies with heterophilic human serum. The interference of human chimeric (diamonds) and murin monoclonal antibodies (squares) and the negligible interference of chimeric avian monoclonal antibodies (triangles and crosses) were analysed by ELISA.

DETAILED DESCRIPTION OF THE INVENTION

The present invention relates to (chimeric) bivalent antibody constructs comprising at least one avian constant domain selected from the group consisting of $C_H2$, $C_H3$, or $C_H4$ avian, in particular, IgY, domains. These constructs comprise recombinant, covalently stabilized bivalent IgY antibodies or truncated bivalent IgY antibody constructs, the format of all of which can be homodimeric or heterotetrameric. Avian IgY, the equivalent of mammalian IgG, is the major low molecular weight serum immunoglobulin in oviparous (egg laying) animals. It is called IgY rather than IgG to distinguish it from its mammalian counterpart (Leslie G A, Clem L W, J Exp Med 130, 1337-1352, 1969). The overall structure of IgY is similar to mammalian IgG, with two light and two heavy chains. The light chain is lighter and the heavy chain of the IgY molecule is larger than its mammalian counterpart. The molecular mass has been reported to be approx. 167 kDa, slightly larger than IgG (approx. 160 kDa) (Sun S, et al., Rapid Commun Mass Spectrom 15, 708-712, 2001). The H chain (approx. 65 kDa), called upsilon (υ, capital letter Y) has one variable (V) region and four constant (C) regions. The light chain (approx. 18 kDa) is composed of one variable and one constant domain. The valency of IgY is two, same as for mammalian antibodies (Warr G W, et al., Immunol Today 16, 392-398, 1995). In place of the hinge region of mammalian IgG, IgY has a more rigid structure, giving IgY limited flexibility. This probably is the reason for many of the different properties of chicken IgY in comparison to mammalian IgG. The restricted mobility of the hinge region (Cυ2) in IgY heavy chain affects the capability of the antibody to precipitate or agglutinate antigens. The Cυ3 and Cυ4 of the IgY are most closely related to the Cγ2 and Cγ3 of IgG, respectively, and the Cυ2 domain is absent in the γ-chain. The Cυ2 region was probably condensed to form the hinge region of IgG as studies have shown that IgY is an ancestor to mammalian IgG and IgE and also to IgA (Warr G W, et al., Immunol Today 16, 392-398, 1995).

In the context of the present invention, an antibody construct has a Y-like structure. It comprises at least one constant domain from the Fc region of an antibody, as the "stem" region of the construct. It further comprises two binding sites, in the "arms" of the construct. As a result of their bivalent binding capability, the affinity of these dimeric molecules is significantly higher than that of corresponding monomeric antibody fragments, a fact that provides significant advantages for the application of the antibody constructs for diagnostic and therapeutical approaches.

An IgY constant domain in the context of the invention refers to an immunoglobulin domain that has a homology of at least 50%, preferably at least 70%, more preferably at least 80% or at least 90%, most preferred at least 95% amino acid homology to the corresponding IgY domain. Thus, e.g., one, two or three amino acids can be deleted, inserted or substituted. In particular, conservative substitutions are contemplated. The boundaries between the domains are preferably defined as by the conserved domain retrieval tool (Geer et al., 2002), however, they can also be shifted, as long as the immunoglobulin domain as a whole is functional.

Due to the phylogenetic difference between avian IgY and mammalian IgG, antibody constructs comprising IgY constant domains provide several important advantages for diagnostic and therapeutical applications. One important advantage is the lack of cross-reactivity with mammalian antibodies. Utilizing mammalian antibodies as secondary anti-mammalian IgG antibodies for immunological detection procedures, these antibodies can cross-react with IgG that is present in a histological section or with bovine IgG in the bovine serum albumin solution often used for blocking purposes. Because chicken IgY is so different from mammalian IgG, cross-reactivity between the two is minimized. Contrary to an anti-mammalian IgG antibody, a secondary anti-chicken IgY antibody will not react with mammalian IgG in the tissue or ELISA well and, thereby, reduces background binding (Larsson A, Lindahl T, Avian immunology in progress, pp. 97-102, INRA Paris 1993). Furthermore, the use of IgY minimizes problems due to the presence of anti-mammalian antibodies in human sera.

Another important advantage of the phylogenetic difference between avian and mammalian species is the lack of human complement activation by IgY antibodies. Because the constructs of the invention do not activate the human complement system, they can be used in diagnostic assays to reduce interference by complement activation (Larsson A, et al., J Immunol Methods 156, 79-83, 1992).

Still another important advantage of the phylogenetic difference between avian and mammalian species is the lack or minimisation of interaction of the construct of the invention with the rheumatoid factor (RF) and human anti-mouse IgG antibodies (HAMA). The IgY constant domains do not interact with RF or HAMA and can thus be used to avoid interference due to these factors (Larsson A, et al., Clin Chem 37, 411-414, 1991; Larsson A, Mellstedt H,. Hybridoma 11, 33-39, 1992).

In addition to the above mentioned advantages, IgY antibodies, and the antibody constructs of the invention, do not interact with human Fc receptors which are found on many types of blood cells (van de Winkel J G, Capel P J, Immunol Today 14, 215-221, 1993). No platelet activation or cytokine production was observed when chicken antibodies were used (Lindahl T L, et al., Thromb Haemost 68, 221-225, 1992). The use of the antibody constructs of the invention will also avoid these problems (Lindahl T L, et al., Thromb Haemost 68, 221-225, 1992).

Furthermore, the use of IgY constant domains also eliminates unwanted bacterial Fc-receptor interactions. The antibody constructs of the invention do not react with protein A or protein G or further bacterial proteins with IgG binding capabilities, and can be used to reduce interference problems due to bacterial Fc receptors (Guss B, et al., EMBO J 5, 1567-1575, 1986; Fischer M, Hlinak A, Berl Munch Tierarztl Wochenschr 113, 94-96, 2000; Hoffman W L, et al., J Immunol Methods 198, 67-77, 1996).

The phylogenetic difference of avian IgY antibodies to IgG antibodies of mammalian origin, and the use of IgY constant domains in the antibody constructs of the invention thus provides several important advantages for diagnostic and therapeutical applications including the lack of cross-reactivity with mammalian antibodies, the lack of human complement activation, and the lack of interaction with human anti-mouse antibodies, the rheumatoid factor, and Fc receptors of human and bacterial origin.

While natural IgY antibodies also avoid many of the disadvantages caused by use of mammalian antibodies or antibodies with IgG constant domains, there are also major limitations to the use of natural IgY. One major problem is the lack of monoclonal IgY antibodies. Currently, only polyclonal chicken egg-derived IgY antibodies are utilized. Although polyclonal IgY antibodies are easy to obtain in relatively large quantities (a hen usually lays about 280 eggs per year, and each egg yolk contains 100-150 mg IgY), they suffer from the known disadvantages of polyclonal antibodies including varying specificities and affinities of different antibody batches. Recently, a chicken monoclonal IgY that recognizes the N-terminal residues of the mammalian prion protein (PrP) was developed by cell fusion (Matsuda H, et al., FEMS Immunol Med Microbiol 23, 189, 1999). However, the chicken hybridoma proved to be very inefficient when compared to murine hybridoma. Only small amounts of chicken antibody were produced. Since the few avian hybridoma cell lines available at present (Nishinaka et al., 1989; Nishinaka et al., 1991; Nishinaka et al., 1996) show similar characteristics, there is a need for monoclonal antibodies that can be produced in large quantities for diagnostic and therapeutical applications. The antibody constructs of the present invention thus also provide significant advantages over the use of natural IgY molecules.

Preferred Constructs

In the context of the invention "IgY antibody construct" refers to bivalent IgY antibodies or truncated bivalent IgY antibody constructs, avian heterotetrameric (FIG. 1) and homodimeric IgY antibodies (FIG. 2) comprising IgY constant domains and avian variable regions derived from libraries, chimeric heterotetrameric (FIG. 3) and chimeric homodimeric (FIG. 4) antibody constructs comprising IgY constant domains and mammalian variable regions, chimeric antibody constructs comprising a combination of mammalian and IgY constant domains and mammalian or avian variable regions (FIG. 5), as well as truncated formats of both entire avian chimeric antibodies and chimeric IgY antibodies derived from different species (FIG. 1-4). Homodimeric antibody constructs comprise single chain variable fragments (scFv) or singular variable regions fused to CH1 domains or to CH2 domains in constructs with deleted CH1 domains. Truncated formats refer to constructs lacking either IgY constant domains CH3 and CH4 or only the CH4 IgY domain. Antibody constructs comprising truncated IgY heavy chains provide a lower molecular mass than complete antibodies, which in many cases has been shown to be associated with increased expression rates.

The invention also includes heterotetrameric bivalent antibody constructs comprising constant and variable domains of avian origin, wherein one or more constant domains are truncated or deleted in relation to the corresponding natural domain(s) or to a natural IgY antibody.

The invention further includes homodimeric bivalent antibody constructs comprising constant and variable domains of avian origin, wherein one or more variable domains are truncated in relation to the corresponding natural domain(s) or to a natural IgY antibody.

The invention also relates to homodimeric and heterotetrameric bivalent antibody constructs comprising constant and variable domains of avian origin, wherein one or more glycosylation sites are deleted in relation to the corresponding natural domain(s) or to a natural IgY antibody.

The constructs of the invention can be monospecific or bispecific, i.e. both binding sites can be specific for the same or for a different molecule. In bispecific antibody constructs the constant domains in the heavy chains are chosen to correspond to each other to allow dimerization. For example, both heavy chains comprise the same number and kind of constant domains.

Preferably, the antibody construct does not comprise a mammalian constant domain from the Fc region, to avoid the above mentioned disadvantages. However, for some applications, it is sufficient if a mammalian constant domain is substituted with an IgY constant domain in the construct, or IgY constant domains are added to avoid particular disadvantages, such as Fc receptor binding, or to reduce crossreactivity. Preferably, the carboxyterminal heavy chain domain of the antibody construct is an IgY domain. The antibody construct can comprise one, two, three or four IgY constant domains. Preferably, the construct comprises $C_H2$, $C_H2$ and $C_H3$, or $C_H2$, $C_H3$ and $C_H4$ IgY constant domains. Other constant domains from the Fc region are preferably deleted.

To ensure bivalent binding, the IgY domain or the IgY domains selected from the group consisting of $C_H2$, $C_H3$, or $C_H4$ IgY domains comprised in the antibody construct of the invention is capable of forming covalently stabilized dimeric molecules. Instead of the conventional domains, fragments or variants thereof that do not inhibit folding or dimerisation of the antibody constructs can be used. The boundaries between the domains, and thus the species origin of fragments at these boundaries can also be varied, as long as folding and dimerisation of the antibody constructs is ensured.

Preferably, the antibody constructs of the invention comprise $V_L$, $V_H$, and $C_H2$-domains (e.g., construct VI, see FIG. 2). This is sufficient to allow dimerization and bivalent antigen binding, as well as detection of the antibody construct by secondary antibodies.

IgY antibody constructs lacking the $C_H3$ and $C_H4$ domains require a stop codon at the 3' boundary of the $C_H2$ domain. However, the potential impact of a stop codon at this position on folding and assembly of such constructs is not predictable due to the particular structural properties of the $C_H2$ domain. While a crystal structure of IgY constant domains is not available, the crystal structure of constant domains of mammalian IgE which is known to be close to chicken IgY in terms of the number of $C_H$ domains, the number of exons and exon lengths as well as the organization of intradomain and interchain disulfide bonds (Warr G W, et al., Immunol. Today 16, 392-398, 1995), has been published recently (Wan T, et al., Nat. Immunol. 3, 681-686, 2002).

The analysis revealed an asymmetrically bent conformation of IgE with the $C_H2$ domains forming highly bent structures at $C_H2$-$C_H3$ junctions. Therefore, truncation of mammalian IgE heavy chains at the $C_H2$ domain is considered likely to fundamentally impair the folding and assembly process of IgE. As a result of the close relationship of mammalian IgE and chicken IgY antibodies, similar considerations apply to IgY antibody constructs lacking the $C_H3$ and $C_H4$ domains. On the other hand, ducks express a truncated version of IgY lacking the $C_H3$ and $C_H4$ domains, but the $C_H2$ domain of this truncated duck antibody exhibits different structural features when compared to those of the $C_H2$ domains of mammalian IgE and chicken IgY. The duck $C_H2$ domain shows structural characteristics of a mammalian hinge region including an abundance of proline residues and several potential interchain disulfide bonds (Parvari R, et al., EMBO J. 7, 739-744, 1988). Furthermore, the $C_H2$ exon of the duck antibody is followed by a terminal exon consisting of nucleic acids encoding EF and a stop codon.

An IgY antibody construct on the basis of chicken sequences was constructed that lacks the $C_H3$ and $C_H4$ domains. In a construct that at the 3' boundary of the chicken $C_H2$ domain comprises the amino acids encoded by the terminal duck exon, EF, it was surprisingly found that these two amino acid residues have a stabilizing effect on the structure of the truncated antibody. Therefore, surprisingly, this novel construct could be expressed in high quantity and correct folding in a covalently stabilized dimeric format. Apparently, the terminal two amino acid residues confer sufficient structural stability to this novel construct. In a preferred embodiment of the invention, the antibody construct thus does not comprise $C_H3$, $C_H4$, or $C_H3$-$C_H4$ domains, but the additional amino acids EF at the carboxyterminal end of the $C_H2$ domain.

In the chimeric antibody constructs of the invention, the binding sites are derived preferably from an antibody and formed by the variable domains of a light and a heavy chain of an antibody, optionally in the form of an scFv. Preferably, variable antibody fragments of mammalian origin are fused to IgY domains capable of forming covalently stabilized dimeric molecules. Preferred fusion protein formats include complete chimeric IgY antibodies with two light and heavy chains (FIG. 4). Also included are bivalent chimeric IgY antibodies with truncated IgY Fc fragments (FIG. 4), bivalent constructs containing single-chain Fv fragments of non-avian origin fused to IgY constant domains or fragments thereof (FIG. 5), and bivalent constructs containing singular variable regions of non-avian origin fused to IgY heavy chain constant regions or fragments thereof. Preferred chimeric IgY antibody constructs capable of forming covalently stabilized dimeric molecules, comprise, in addition to IgY heavy chain constant domains, non-avian, preferably mammalian variable antibody fragments and a non-avian, preferably mammalian light chain constant domain. Such constructs may comprise all IgY heavy chain constant domains or only a fraction of them. Other preferred chimeric IgY antibody constructs capable of forming covalently stabilized dimeric molecules, comprise, in addition to IgY heavy chain constant domains, non-avian, preferably mammalian variable antibody fragments, a non-avian, preferably mammalian light chain constant domain, and a $C_H1$ domain of non-avian, preferably mammalian origin. Such constructs may comprise the three IgY constant domains $C_H2$, $C_H3$, and $C_H4$ or only one ($C_H2$) or two ($C_H2$ and $C_H3$) of these domains. Still other preferred chimeric IgY-derived constructs capable of forming covalently stabilized dimeric molecules, include bivalent constructs containing single-chain Fv fragments of non-avian, preferably mammalian origin fused to IgY constant domains or fragments thereof. Preferred chimeric IgY-derived constructs capable of forming covalently stabilized dimeric molecules also include bivalent constructs containing singular variable regions of mammalian origin fused to IgY heavy chain constant regions or fragments thereof.

Constructs with a Higher Resistance to Acidic Conditions

One of the major limitations of conventional IgY antibodies for therapeutic applications is their reduced stability to acid denaturation when compared to mammalian IgG. After incubation under acidic conditions for 7 hours at 37° C., the antigen binding activity of IgY was found to decrease significantly at pH 3.5 and to be abolished at pH 3.0 (Shimizu M, et al., Biosci Biotech Biochem 56, 270-274, 1992). In contrast, under identical conditions the antigen binding activity of IgG did not change significantly until the pH was decreased to pH 2.0, and even at this pH a decrease of less than 20% in antigen binding activity was observed. Since a similar difference in stability of the antigen binding region to acid denaturation was also noticed for other antigen-specific IgY and corresponding mammalian IgG antibodies (Shimizu M, et al., Biosci Biotech Biochem 56, 270-274, 1992), the data cannot be attributed to the structural properties of a particular type of antigen binding region. As demonstrated by circular dichroism (CD) analyses, the loss of antigen binding activity of IgY upon incubation under acidic conditions is accompanied by significant conformational changes (Shimizu M, et al., Biosci Biotech Biochem 56, 270-274, 1992). The CD spectrum of IgY at pH 2 revealed a marked destruction of its secondary structures. These changes were much smaller in rabbit IgG indicating a more rigid and stable conformation of rabbit IgG under acidic conditions. As a result of this low stability under acidic conditions, IgY antibodies suffer severe damage when subjected to the conditions of most conventional purification processes which have been used successfully for IgG of mammalian origin (U.S. Pat. No. 4,550,019). Furthermore, for oral delivery of IgY antibodies the acidic pH of the stomach represents a serious limitation. In newborns, the gastric fluid has a pH close to neutral, but during the first days the pH rapidly decreases below pH 3, which will denature therapeuctically administered IgY antibodies. Therefore, there is a need in the field to generate monoclonal IgY antibodies or IgY-derived antibody constructs that are more stable under acidic conditions.

The combination of IgY constant domains with variable and selected constant domains of mammalian monoclonal antibodies allows the design of antibody constructs which exert a higher resistance to acidic conditions than natural IgY antibodies.

The IgY-derived constructs of the instant invention which exert higher resistance to acidic conditions comprise constant domains of the IgY heavy chain and mammalian immunoglobulin domains identified to be important for a higher molecular stability of IgG antibodies under acidic conditions. Such IgY-derived antibody constructs suffer significantly less damage when subjected to the conditions of most conventional purification processes and are more suitable for oral delivery.

Preferred IgY-derived constructs exerting a higher resistence to acidic conditions contain $V_L$ and $C_L$ domains of mammalian origin, derived from κ or λ-chains, which are stabilized by an additional disulfide linkage between the $V_L$ and $C_L$ domains. This type of intrachain disulfide linkage is not present in the IgY L-chain. The importance of intrachain disulfide linkages for stabilization of immunoglobulin-domains has been demonstrated in several studies (Goto Y, and Hamaguchi K, J. Biochem. 86, 1433-1441, 1979; Ashikari Y, et al., J Biochem 97, 517-528, 1985). For example, the stability of an intact $C_L$ fragment of human origin under acidic conditions was 100 times higher than that observed for the reduced $C_L$ domain (Ashikari Y. et al., J Biochem 97, 517-528, 1985). Other preferred constructs exerting a higher resistance to acidic conditions also comprise $V_H$ and $C_H1$ domains of mammalian origin. Thereby, the content of stabilizing β-structures is increased, since mammalian constant domains contain more β-sheet structures than those of IgY. For example, IgY $C_H1$ domains contain 25% β-sheet structures, rabbit IgG $C_H1$ domains 40% (Shimizu M, et al., Biosci Biotech Biochem 56, 270-274, 1992). Similarly, IgY $C_L$ domains contain 33% β-sheet structures, rabbit IgG $C_L$ domains 47% (Shimizu M, et al., Biosci Biotech Biochem 56, 270-274, 1992). Other preferred constructs exerting a higher resistence to acidic conditions contain a mammalian hinge region. The lack of a hinge region in IgY antibodies limits their flexibility, thereby adding to the molecular instability of IgY under acidic conditions. Preferably, the antibody construct comprises $V_H$, $V_L$, $C_L$, $C_H1$, and $C_H2$ domains, wherein the $V_H$, $V_L$, $C_L$, and $C_H1$ domains as well as the hinge region are of mammalian origin.

Non-Glycosylated and Mono-Glycosylated Antibody Constructs

Another major limitation for diagnostic and therapeutic applications is the interaction of mammalian immunoglobulins and IgY antibodies via their oligosaccharide chains with C-type lectins in human sera and other human body fluids. C-type lectins bind sugars in a calcium-dependent manner via highly conserved carbohydrate recognition domains (CRD). C-type lectins are either produced as transmembrane proteins, e.g., on dendritic cells and Langerhans cells (for a review, see Figdor C G, et al., Nature Rev. Immunol. 2, 77-84, 2002), or secreted as soluble proteins. Examples of soluble C-type lectins include the mannan-binding lectin (MBL), the surfactant protein A (SP-A) and D (SP-D), and the conglutenins CL-46 and CL-43, all of which belong to the collectin family (for a review, see Van de Wetering J K., et al., Eur. J. Biochem. 271, 1229-1249, 2004). MBL is secreted into the blood stream. The presence of substantial amounts of MBL in the small intestine suggests that this protein is acting as a humoral immune factor in the intestine, similar to secretory IgA. SP-A and SP-D are secreted at the luminal surface of pulmonary epithelial cells, and recently an increased expression of SP-D in the gastric mucosa during *Heliobacter pylori* infection has been reported, pointing to a role of the surfactant proteins in mucosal defense systems. The serum collectins conglutenin CL-46 and CL-43 have so far only be detected in bovidae, where the liver is their main site of production. The basic functional unit of collectins is a trimer, but the number of trimeric units per collectin molecule differs among the collecting. MBL and SP-A form octadecamers of six trimeric subunits, with their overall structure resembling a bouquet of flowers, whereas SP-D and the bovine conglutein proteins are assembled into dodecamers of four trimeric subunits. In addition, SP-D can form even higher-order multimers with a mass of several million kDa. The size of fully assembled collectins ranges from 13 nm for MBL to about 100 nm for SP-D. In order to recognize a variety of cell surface saccharides, collectins provide a broad monosaccharide specificity including mannose, galactose, and glucose. Although the $K_d$ of the binding of a single CRD with a monosaccharide ligand is in the order of $10^{-3}$ M., the $K_d$ of binding of higher-order multimers of collectins to polyvalent ligands is in the order of $10^{-8}$ to $10^{-11}$ M. As a result, IgY and mammalian immunoglobulins can be bound tightly via their oligosaccharide chains by collecting. For example, MBL has been shown to bind agalactosylated glycoforms of IgG (Malhotra R., et al. Nat. Med. 1, 237-243, 1995) and to polymeric forms of serum IgA (Roos A., et al. J. Immunol. 167, 2861-2868, 2001). In chicken IgY, each H-chain contains two potential N-glycosylation sites located on $C_H2$ (Asn308) and CH3 (Asn407) domains. The CH2 domain contains biantennary complex-type N-glycans (neutral, 29.9%; monosialyl, 29.3%; disialyl, 3.7%), whereas the CH3 domain contains high-mannose-type oligosaccharides (monoglucosylated, 26.8%; others, 10.5%) (Suzuki N, Lee Y C, Glycobiology 14, 275-292, 2004). The structural properties of complex-type N-glycans from chicken IgY resemble those of human IgG (Suzuki N, et al., J. Biol. Chem. 278, 46293-46306, 2003). Both human IgG and chicken IgY possess biantennary complex-type oligosaccharides with and without core aplha 1-6 Fuc and/or bisecting GlcNAc. Both antibodies have a mono-galactosylated branch predominantly on the GlcNAc beta 1-2 Man alpha 1-6 Man arm. Monosialylation in chicken IgY occurs on the Gal beta 1-4 GlcNAc beta 1-2 Man alpha 1-3 Man arm, which is also the case in normal human IgG (Takahashi N, et al., Anal. Biochem. 226, 139-146, 1995). Due to these similarities, N-glycans of IgY antibodies pose similar problems as those of human and other mammalian antibodies. In ELISA-type diagnostic procedures, the presence of soluble C-type lectins in sera of patients can lead to false positive results as described for RF and HAMA (Boscato L M, Stuart M C, Clin Chem 34, 27-33, 1988). For example, most capture antibodies and many proteins utilized for coating or blocking of a solid phase in ELISA-type assays are glycoproteins which will bind soluble C-type lectins upon exposure to patient's sera. Since many C-type lectins such as MBL form oligomers of trimeric subunits, bound C-type lectins are likely to provide additional binding sites for glycosylated detection antibodies which could result in false positive data. Intestinal C-type lectins may also affect the efficacy of orally administered IgY antibodies for the treatment of gastrointestinal infections. For example, the presence of substantial amounts of MBL in the small intestine could result in a significant reduction of administered IgY antibodies that remain available for interaction with infectious agents. Therefore, there is a need in the field for monoclonal antibodies or fragments thereof which do not interact with C-type lectins.

The present invention provides IgY antibody constructs comprising one ore more deleted glycosylation sites. Glycosylation of only one potential site on IgY constant domains reduces interference by C-type lectins in diagnostic and therapeutic applications, and is likely to help folding, assembling, and secreting such constructs in eukaryotic cells. One line of evidence for this assumption is the observation that glycosylation site Asn407 of IgY antibodies is well conserved in mammalian IgG (Asn297) and mammalian IgE (Asn394) although the number and position varies among the different species (Suzuki N, Lee Y C, Glycobiology 14, 275-292, 2004). Structural analyses of constant domains of mammalian IgE and IgG have demonstrated that N-glycans on Asn394 (mammalian IgE) and Asn297 (mammalian IgG) are buried in a cavity between the two heavy chains. Although the function of N-glycans in the cavity between the two heavy chains of mammalian IgE, IgG, and avian IgY remains to be elucidated, they probably play a role in folding, assembly, and stabilization of the immunoglobulin structures. Human IgE lacking N-glycosylation at Asn394 by point mutation has been reported to tend to self-aggregration (Basu M, et al., J. Biol. Chem. 268, 13118-13127, 1993), suggesting that N-glycans at this position are involved at least in stabilization of the protein structure by conferring suitable hydrophilicity to the cavity (Suzuki N, Lee Y C, Glycobiology 14, 275-292, 2004). Therefore, mono-glycosylation of IgY constant domains can be expected to help folding, assembling, and secreting such constructs in eukaryotic cells.

However, it has surprisingly been found that the antibody constructs of the invention are correctly folded and secreted, even if both gylcosylation sites are deleted (constructs XVI, XX, XXIII, see FIGS. 6 and 7). In one embodiment, the antibody constructs are thus non-gylcosylated. The absence of N-glycans on all of these antibodies and antibody constructs guarantees a lack of interference by C-type lectins in diagnostic and therapeutic applications. Compared to glycosylated IgY and mammalian antibodies, non-glycosylated bivalent recombinant IgY-related constructs provide a higher degree of reliability in diagnostic assay procedures and a higher therapeutic efficacy when orally administered.

Preferred non-glycosylated bivalent antibody formats include a) recombinant IgY antibodies and related constructs comprising IgY domains only, and b) chimeric IgY antibody constructs comprising also non-IgY domains. Ad a) Non-glycosylated IgY antibodies and related constructs comprising IgY domains include complete IgY antibodies that mirror their natural counterpart, bivalent antibodies with truncated IgY Fc fragments, bivalent constructs containing single-chain Fv fragments of avian origin fused to IgY constant domains, and bivalent constructs containing singular variable regions of avian origin fused to IgY heavy chain constant regions. Ad b) Non-glycosylated chimeric IgY antibody constructs include complete bivalent antibodies, bivalent antibodies with truncated Fc fragments, bivalent constructs containing single-chain Fv fragments fused to constant domains, and bivalent constructs containing singular variable regions fused to heavy chain constant regions. The different immunoglobulin domains of the chimeric constructs are of avian and non-avian, preferably mammalian, origin as described above.

Other preferred fusion protein formats of this part of the invention include c) IgY antibodies and related constructs comprising IgY domains only, and d) chimeric IgY antibody constructs comprising non-IgY domains, in all of which the IgY constant domains are only mono-glycosylated, either on Asn308 (CH2 domain) or on Asn407 (CH3 domain). Ad c) Mono-glycosylated IgY antibodies and related constructs comprising IgY domains only include complete IgY antibodies that mirror their natural counterpart, bivalent antibodies with truncated IgY Fc fragments, bivalent constructs containing single-chain Fv fragments of avian origin fused to IgY constant domains, and bivalent constructs containing singular variable regions of avian origin fused to IgY heavy chain constant regions. Ad d) Mono-glycosylated chimeric IgY antibodies and related constructs include complete bivalent antibodies, bivalent antibodies with truncated Fc fragments, bivalent constructs containing single-chain Fv fragments fused to constant domains, and bivalent constructs containing singular variable regions fused to heavy chain constant regions. The different immunoglobulin domains of the chimeric constructs are of avian and non-avian, preferably mammalian, origin as described above.

Variable Domains

Preferably, the antibody construct of the invention is chimeric, i.e., it comprises parts from one species and parts from another species, or parts from one species and parts from a library, in particular a semisynthetic or synthetic library. The construct can also be derived from more than two species, e.g. from three species. Minimally, the part from one species comprises two amino acids, e.g., in case of a chicken-duck chimera without $C_H3$-$C_H4$ domains, but with the carboxyterminal EF motive from duck, as discussed above. In any case, the construct is recombinantly expressed and differs from a natural antibody.

Preferably, at least the variable domains are derived from a non-avian species. The combination of IgY constant domains with variable domains of monoclonal antibodies of non-avian origin allows the design of antibody constructs which exhibit antigen binding characteristics of established monoclonal antibodies that have been demonstrated to be useful for diagnostic procedures. Such antibody constructs can save both time and money, since the development of monoclonal antibodies that are useful for diagnostic procedures with regard to specificity and affinity can be very time-consuming and costly.

The variable antibody fragments of chimeric IgY antibody constructs can be of mammalian origin, e.g., from mouse, rat, rabbit or human origin, or derived from any other non-avian species. Preferably, variable antibody fragments of existing monoclonal antibodies are utilized, which are known to be useful for diagnostic or therapeutical applications. However, variable antibody fragments also may be generated from hybridoma cells, from synthetic or semisynthetic immunoglobulin libraries or from those built from lymphoid sources. Immortalised B-cells can provide variable regions with specificity for all kinds of target molecules. Hybridoma technology nowadays is well established for producing murine monoclonal antibodies. Rodent hybridomas serve as the origin of the majority of available monoclonal antibodies. Consequently, the majority of available monoclonal antibodies are murine. Generation of human hybridomas from donors without prior immunisation, although reported, remains high in effort. Primed antibody repertoires can be generated from lymphoid cells of immunised donors (Clackson et al., 1994) of various species such as human, mouse, rabbit, camel, etc. (Barbas et al., 1993; Davies et al., 1995; Lang et al., 1996, Arbabi Ghahroudi et al., 1997). However, non-primed antibody repertoires can also yield antibodies against all types of antigens. Such single-pot libraries can be constructed either using lymphoid cells of non-immunised donors (Marks et al., 1991) or artificially by in vitro assembly of V-gene segments and D/J-segments (Barbas et al., 1992; Hoogenboom et al., 1992). Due to different length of CDR and introduction of mutations random wisely or in defined areas, these libraries significantly vary in diversity (Nissim et al., 1994). In general, generation of libraries of other species than human is less complicated. Many domesticated species predominantly express lamda light chains, provide repertoires found in single gene families or generated by diversification of single V-genes. These properties render the cloning of antibody reperoires more efficient and resulting libraries exhibit broader diversity. Preferably, the non-avian variable domains are scFv.

In an alternative embodiment, the antibody construct of the invention comprises variable domains of avian origin. The phylogenetic difference between avian and mammalian species provides access to a different antibody repertoire than the traditional mammalian antibodies. IgY antibodies recognize other epitopes than mammalian antibodies. Furthermore, IgY antibodies raised against mammalian proteins in chicken are known to bind to more epitopes than corresponding mammalian antibodies. For example, it has been shown that 3-5 times more chicken antibody than swine antibody will bind to rabbit IgG which will amplify the signal in an immunological assay (Horton J, et al., J Invest Dermatol 85, 96-99, 1984; Olovsson M, Larsson A, Comp Immunol Microbiol Infect Dis 16, 145-152, 1993). In addition, for the production of antibodies against conserved mammalian proteins chicken is a better choice than e.g. rabbits, since the immune response usually increases as the difference between the antigen and the immunized animal increases (Horton J, et al., J Invest Dermatol 85, 96-99, 1984; Song C S, et al., J Immunol 135, 3354-3359, 1985).

In the context of the invention avian variable domains are derived preferably from synthetic or semisynthetic avian immunoglobulin libraries. Such libraries provide a higher diversity than those displaying only naturally occurring variable domain sequences.

Recombinant antibody libraries of high diversity are technically even easier to generate from chickens than from mammalian species such as mice, due to the peculiar mechanism of immunoglobulin gene diversification in birds. Chickens possess only one functional immunoglobulin heavy chain variable region ($V_H$) gene and one light chain variable region ($V_L$) gene from which diversity is created by gene conversions involving immunoglobulin gene rearrangements and recombination with a number of non-functional pseudogenes. Approximately 25 $V_L$ pseudogenes upstream of the $V_L$ gene and up to 100 $V_H$ pseudogenes upstream of the $V_H$ gene contain sequences similar to the single $V_L$ or $V_H$ genes, but lack other functional elements including the promotor region. Single primers designed around the conserved regions flanking the unique functional $V_L$ and $V_H$ genes can therefore be used to amplify by polymerase chain reaction (PCR) the complete spectrum of rearranged variable fragments.

Using the phage display technology, scFv as well as Fab libraries of chicken immunoglobulin genes have been constructed (Davies E L, et al., J Immunol Meth 186, 125-135, 1995; Yamanaka H I, et al., J Immunol 157, 1156-1162, 1996; Andris-Widhopf J, et al., J Immunol Meth 242, 159-181, 2000; Sapats S I, et al., Arch Virol 148, 497-515, 2003; Nakamura N, et al., J Immunol Meth 280, 157-164, 2003). For constructs of the invention the variable domains are preferably scFv.

The variable antibody fragments of avian origin are fused to IgY domains capable of forming covalently stabilized bivalent molecules (FIG. 1). Other preferred fusion protein formats include bivalent constructs containing single-chain Fv fragments of avian origin fused to IgY constant domains or fragments thereof (FIG. 2). Other preferred fusion protein formats include bivalent constructs containing singular variable regions of avian origin fused to IgY heavy chain constant regions or fragments thereof.

In one particular embodiment, the invention relates to recombinantly produced complete avian or IgY antibodies. Preferably the domains of avian origin or IgY domains are of chicken or duck origin or chicken-duck chimeric origin. In particular, throughout the invention, the domains of avian origin are derived from IgY. The variable domains are derived preferably from synthetic or semisynthetic avian immunoglobulin libraries which provide a higher diversity than those displaying only naturally occurring variable domain sequences. Semisynthetic avian immunoglobulin libraries are produced by in vitro random mutagenesis of naturally occurring complementarity determining regions (CDR) which artificially increases the diversity by several orders of magnitude. Synthetic avian immunoglobulin libraries are generated by in vitro assembly of V-gene segments and D/J-segments (Barbas et al., 1992; Hoogenboom et al., 1992) utilizing artificially derivatized V-genes. Due to the different length of CDR introduced by incorporation of random synthetic oligonucleotides into CDR sections, such libraries provide a diversity of up to $10^{11}$ and, thereby, provide coding sequences for approximately $10^3$ to $10^4$ variable regions that do not occur in nature. By using synthetic or semisynthetic avian immunoglobulin libraries for the construction of complete IgY antibodies, these antibodies provide antigen binding regions that contain non-avian, synthetic CDR sequences and, thereby, are different from naturally occurring avian monoclonal antibodies.

Nucleic Acids and Expression System

The present invention also provides nucleic acid sequences and vectors encoding the above listed monoclonal IgY antibodies and the antibody constructs of the invention. To produce the antibody constructs, one having ordinary skill in the art can prepare a DNA molecule encoding the antibody construct using well known techniques. The coding sequence can be obtained from natural sources or synthesized or otherwise constructed using widely available starting materials by routine methods. In some embodiments, a DNA molecule that includes a nucleotide sequence that encodes an antibody construct of the invention may be synthesized using the amino acid sequence information herein (FIG. 8) and the genetic code. When the coding DNA is prepared synthetically, advantage can be taken of known codon preferences of the intended host where the DNA is to be expressed. One having ordinary skill in the art can insert that DNA molecule into a commercially available expression vector for use in well known expression systems, employing well known methods and readily available starting materials (see e.g., Sambrook et al., Molecular Cloning. A Laboratory Manual, second ed., Cold Spring Harbor Press, 1989).

In another embodiment, the present invention provides expression systems suitable for the production of the above listed monoclonal IgY antibodies and antibody constructs. Expression of these requires eukaryotic systems which provide a variety of processing mechanisms in the endoplasmatic reticulum (ER), including chaperone-assisted folding, optionally, glycosylation and oxidation. In principle, immortilized chicken cells represent the first choice for the expression of chicken IgY antibodies. However, available immortilized chicken (*Gallus gallus*) cells are associated with several disadvantages. Some of them have been transformed by viral infection, a fact that may cause problems if the recombinant IgY antibodies are utilized for therapeutic applications. Other chicken cell lines derived from B lymphocytes are not suitable, since they express their own immunoglobulins. Several chicken cell lines are derived from embryos and may provide only a limited doubling potential as described the embryonic CRL-1590 cell line (Ramirez A D, et al., J. Eukaryot. Microbiol. 42, 705-708, 1995). A general disadvantage of all chicken cell lines is the lack of standardized protocols for mass production of recombinant immunoglobulins in avian cells. On the other hand, such protocols are existent for non-avian eukaryotic cells, including but not limited to chinese hamster ovary (CHO) cells and human embryonic kidney (HEK) cells. These cells are widely used for mass production of recombinant mammalian immunoglobulins. In mammalian cells, however, the interaction of chaperones with nascent immunoglobulin chains is crucial for the proper assembly and transport of antibodies. To date more than 10 chaperones, as well as numerous regulators and co-factors for these chaperones, have been identified in the mammalian ER (for a review, see Hendershot L A, Mount Sinai J. Med. 71, 289-297, 2004). Especially, the role of the chaperone BiP in the folding process of IgG antibodies has been elucidated in detail. Although the overall structure of the different immunoglobulin domains is extremely similar, the folding requirements and dependence on BiP are very different. BiP binds transiently to most $C_H$ domains and some $V_H$ and $V_L$ domains (Knittler M R, Haas I G, EMBO J. 11, 1573-1581, 1992; Hendershot L, et al., Proc. Natl. Acad. Sci. USA 93, 5269-5274, 1996). The $C_H1$ domain, which pairs with the $C_L$ domain of the light chain and provides the site for its covalent attachment, interacts stably with BiP in the absence of light chains (Hendershot L, et al., J. Cell Biol. 104, 761-767, 1987). The interaction of this domain with BiP is crucial to controlling immunoglobulin assembly and transport, since deletion of this domain and the resulting lack of interaction with BiP leads to secretion of unassembled and partially assembled immunoglobulin intermediates (Hendershot L, et al., J. Cell Biol. 104, 761-767, 1987). The different interaction of BiP with heavy and light chain domains demonstrates that chaperone-assisted folding of immunoglobulins requires sequence and structure specific interaction of involved chaperones with nascent immunoglobulin chains. Based on these data, mammalian ER chaperones were considered not to be capable to bind specifically to avian immunoglobulin chains since the sequence homology of constant domains of mammalian and avian antibodies is marginal (FIG. 9). This assumption is further supported by the lack of interaction of IgY antibodies with mammalian Fc- and complement receptors, anti-mammalian immunoglobulin antibodies, RF, protein A and G, and by their inability to activate mammalian complement. Since a lack of interaction with BiP leads to secretion of unassembled and partially assembled immunoglobulin intermediates, expression of bivalent avian antibodies and related bivalent constructs in eukaryotic cells of non-avian origin should lead also to incomplete assembly of avian antibodies.

Surprisingly, however, non-avian cells, in particular, mammalian HEK cells, proved to be capable of expressing and secreting immunoreactive monoclonal IgY antibodies, fragments thereof, and scFv-IgY antibody constructs in a covalently stabilized bivalent format. Based on this surprising observation, HEK cells were also employed for the expression of the chimeric IgY antibodies and related constructs of the present invention. HEK cells proved to be capable of also expressing and secreting the chimeric IgY antibody constructs in a covalently stabilized bivalent format. All of the expressed and secreted chimeric constructs exhibit immunoreactivity.

The present invention thus also relates to recombinant IgY antibodies or the antibody construct of the invention, expressed in mammalian cells, as well as to a method of expressing recombinant IgY antibodies or the antibody construct of the invention in eukaryotic cells, in particular, non avian cells. Several eukaryotic hosts including commonly used yeast, fungal cells, insect cells, mammalian cells, and cells of higher plants, are available for the production of the antibody constructs. The particulars for the construction of expression systems suitable for the desired host are known to those in the art.

Based on the surprising observation that truncated IgY antibody constructs comprising a short sequence of a duck exon at the C-terminus of the $C_H2$ domain could be expressed in a covalently stabilized bivalent format in HEK cells, truncated chimeric IgY antibody constructs lacking the $C_H3$ and $C_H4$ domains were also equipped at the 3' terminus of the $C_H2$ domain with this sequence consisting of EF and a stop codon. These truncated chimeric IgY antibody constructs could be expressed in a covalently stabilized bivalent format in HEK cells.

The present invention also provides nucleic acid sequences, vectors and expression systems encoding the above listed non-glycosylated or mono-glycosylated constructs. The potential glycosylation sites can be eliminated by site-directed mutation using well known techniques. HEK cells were also employed for the expression of the non-glycosylated and mono-glycosylated constructs listed above. HEK cells proved to be capable of expressing and secreting both non-glycosylated and mono-glycosylated constructs in a covalently stabilized bivalent format. None of the secreted antibody constructs exhibited a tendency to self-aggregation. Both non-glycosylated and mono-glycosylated IgY antibody constructs proved to be immunoreactive. Non-glycosylated IgY antibodies and the constructs comprising truncated IgY heavy chains provide an additional advantage in that the molecular mass of a recombinant protein frequently shows an inverse relationship to its expression rate.

Since truncated IgY antibody constructs containing at the C-terminus of the $C_H2$ domain a short sequence of a duck exon, could be expressed in a covalently stabilized bivalent format in HEK cells, sequences encoding both non-glycosylated and mono-glycosylated truncated IgY-derived antibody constructs lacking the $C_H3$ and $C_H4$ domains were also equipped at the 3' terminus of the $C_H2$ domain with the sequence encoding EF and a stop codon. HEK cells proved to be capable of expressing and secreting both non-glycosylated and mono-glycosylated truncated IgY-derived constructs in a covalently stabilized bivalent format.

In summary, mammalian cells are suitable for the expression and secretion of a variety of monoclonal IgY antibodies and all chimeric IgY antibody constructs of the invention.

The present invention therefore relates to a nucleic acid molecule encoding the antibody construct of the invention, as well as an expression vector comprising this nucleic acid molecule under control of an appropriate promoter. The invention also relates to a host cell comprising this expression vector, in particular a mammalian cell.

Diagnostic and Pharmaceutic Applications

The antibody construct of the invention can advantageously be used for in vitro diagnostic purposes or for the preparation of a pharmaceutical composition. The invention also relates to a diagnostic agent or a pharmaceutical composition comprising the antibody construct of the invention. In particular the pharmaceutical composition is for peroral administration.

Since IgY antibodies neither activate mammalian complement nor interact with Fc- and complement receptors that could mediate inflammatory responses in the mammalian gastrointestinal tract, the chimeric antibody constructs of the invention or the recombinant IgY antibodies of the invention also appear to be well suited for peroral immunotherapy both in humans and animals. Oral administration of antibodies specific to host pathogens is an attractive approach to establish protective immunity, especially against gastrointestinal pathogens. Furthermore, the increasing number of antibiotic-resistant bacteria emphasizes the need to find alternatives that support antibiotics. IgY-mediated immunotherapy may also be used as a complementary treatment against oral and enteric pathogens that are difficult to treat with traditional antibiotics. Systemic effects after oral administration of IgY can be excluded since eggs containing each 100-150 mg IgY are normal dietary components. No absorption of intact IgY antibodies has been shown in humans (Losonsky G A, et al., J Clin Invest 76, 2362-2367, 1985; Blum P M, et al., Pediatr Res 15, 1256-1260, 1981). Although caution should be taken to give IgY to persons with known egg allergy, there is practically no risk of toxic side effects of IgY given orally.

During recent years, oral administration of IgY has proved successful for treatment of a variety of gastrointestinal infections including bovine and human rotaviruses, bovine coronavirus, *Yersinia ruckeri*, enterotoxigenic *Escherichia coli*, *Samonella* spp., *Edwardsiella tarda*, *Staphylococcus*, and *Pseudomonas* (Mine Y, Kovacs-Nolan J, J Med Food 5, 159-169, 2002). A recent phase I feasibility study has also provided evidence that oral administration of specific IgY antibodies may prevent *Pseudomonas aeruginosa* (PA) infections in patients with cystic fibrosis (CF) (Kollberg H, et al., Pediatr Pulmonol 35, 433-440, 2003). CF patients which had gargled daily with anti-PA IgY antibodies, exhibited a significantly decreased degree of PA colonization. Furthermore, oral administration of IgY antibodies with specificity for *Streptococcus mutans* glucan binding protein B has been shown to confer protection against experimental dental caries (Smith D J, et al., Infect Immun 69, 3135-3142, 2001). Anti-cariogenic effects have also been observed in rats after oral administration of IgY antibodies with specificity for *Streptococcus mutans* cell-associated glucosyltransferases (Krüger C, et al., Caries Res 38, 9-14, 2004). The antibody constructs of the invention can be advantageously used for all these applications. Particular advantages are provides by use of those constructs that are mono- or non-glycosylated or more resistant to acidic conditions.

The antibody constructs of the present invention can also be advantageously applied in all in vitro diagnostic methods, as described above, where their use minimizes cross-reactivity and false positive and negative results. Further applications are found, e.g., as research tools or for biotechnological methods, e.g., in protein purification.

In summary, the IgY antibody constructs offer great opportunities for diagnostic applications and for novel therapeutic approaches.

EXAMPLES

A variety of antibody formats including scFv-derived constructs as well as complete antibody constructs are suitable for the present invention. The structure of some of these antibody formats described in the following examples are shown in FIGS. 1-9.

Example 1

Amplification and Cloning of IgY Constructs 1.1 Amplification and Cloning of Entire Avian Heterotetrameric Antibody Constructs For convenient expression of heterotetrameric antibody constructs, a set of modular cassettes was generated. Expression of the heterotetrameric IgY was achieved by inserting the IgY heavy chain and the λ light chain domains simultaneously into the mammalian expression vector pBudCE4.1 (Invitrogen life technologies, Karlsruhe, Germany). Expression of the heterotetrameric IgYΔFc was achieved by inserting the $υC_H1-2$ domains and the λ light chain domains simultaneously into the mammalian expression vector pBudCE4.1 (Invitrogen life technologies, Karlsruhe, Germany). Coexpression of heavy and light chains is driven by strong CMV and EF-1α promoters.

Experimental methods can be carried out following standard methods well known in the art (e.g., Sambrook J, Fritsch E F, Maniatis T. Molecular Cloning. A Laboratory Manual, second ed., Cold Spring Harbor Press, 1989.). In the following examples, if not described otherwise, standard PCR conditions were: hotstart: 3 min 95° C., 30× (30s 95° C., 1 min 55° C., 1 min 72° C.), 5 min 72° C.

1.1.1 Amplification and Cloning of the Human κ Light Chain Leader Sequence

The signal sequence of a human κ light chain together with the anti-IBDV (Infectious bursal disease virus) variable light chain was synthesised by using overlapping primers containing an Sbf I site (ctggggctcctgctactctgcctgca gggtgccagatgt-gcgctgactcagccgtcc, SEQ ID NO:1) and a Sal I site (gatcgtc-gacatggacatgagggtccccgctcagctcctggggctcctgct actc, SEQ ID NO:2) and a primer containing a Sgf I site (gatcgcgatcg-cacctaggacggtcagggttgtccc, SEQ ID NO:3). After hybridisation of the resulting fragments the light chain sequence was introduced via the Sal I and the Sgf I sites into the mammalian expression vector pBudCE4.1 (Invitrogen life technologies, Karlsruhe, Germany).

1.1.2 Amplification and Cloning of the Human Heavy Chain Leader Sequence

The signal sequence of a human immunoglobulin heavy chain together with the anti-IBDV variable heavy chain was synthesised by using overlapping primers containing an Swa I site (tgggttttccttgttgctaggcgcgccatctagagaggagacgatgac, SEQ ID NO:4) and a Not I site (agaatgcggccgcatggaat-tggggctgagctgggttttccttgttgc, SEQ ID NO:5) and a primer containing an Asc I site (gatcggcgcgccagaggagacgatgacttcggt, SEQ ID NO:6). After hybridisation of the resulting fragments the heavy chain sequence was introduced via the Not I and the Asc I sites into the mammalian expression vector pBudCE4.1 (Invitrogen life technologies, Karlsruhe, Germany).

1.1.3 Amplification and Cloning of Chicken Constant Regions for Heterotetrameric Antibodies All chicken immunoglobulin constant domains were synthesised from cDNA derived from chicken splenocytes. The 5' end of the chicken υ heavy chain was amplified using the PCR primer (accgaagtcatcgtctcctc, SEQ ID NO:7) and (cctcagtttggcgtct aagc, SEQ ID NO:8). The 3' end was amplified using the PCR primer (gaggatcacgtcaagggatg, SEQ ID NO:9) and (gcaccccc aatcctttattt, SEQ ID NO:10). After hybridization of these two fragments the complete chicken U heavy chain was amplified using the PCR primer (accgaagtcatcgtctcctc, SEQ ID NO:7) and (gcacccccaatcctttattt, SEQ ID NO:10).

For the IgY construct the υ constant heavy chain was amplified using a primer containing an Asc I site (gatcggcgcgcccgcgagcccacatcgcc, SEQ ID NO:11) and another primer containing a Sfi I site and a 4×His overhang (gatcggcccagccggcctcagtgatggtgatgtttaccagcctgtttctg, SEQ ID NO:12). The υ constant heavy chain was inserted into the mammalian expression vector pBudCE4.1 (Invitrogen life technologies, Karlsruhe, Germany) modified as described above via Asc I and Sfi I.

For the IgYΔFc construct the υ $C_H$1-2 domain was amplified using one PCR primer containing an Asc I site (gatcggcgcgcccgcgagcccacatcgcc, SEQ ID NO:11) and another PCR primer containing a Sfi I site and a 4×His overhang (gatcggcccagccggcctcagtgatggtgatggaactccgggcatcccttgacgtgatc, SEQ ID NO:13). The υ $C_H$1-2 domain was inserted into the mammalian expression vector pBudCE4.1 (Invitrogen life technologies, Karlsruhe, Germany) modified as described above via Asc I and Sfi I.

1.1.4 Amplification and Cloning of the λ Light Chain Sequence

The chicken λ light chain constant domain was amplified from cDNA derived from chicken splenocytes, using one PCR primer containing a Sgf I site (gatcgcgatcgcgcagcccaaggtggcccccac, SEQ ID NO:14) and another primer containing an Xba I site (gatctctagatcagcactcggacctcttcag, SEQ ID NO:15). The constant λ light chain sequence was introduced via the Xba I and the Sal I sites into the mammalian expression vector pBudCE4.1 (Invitrogen life technologies, Karlsruhe, Germany).

1.2 Amplification and Cloning of Avian Homodimeric Antibody Constructs

For convenient expression of scFv-derived homodimeric antibody constructs a set of modular cassettes containing leader sequences, constant immunoglobulin regions, and restriction sites for the incorporation of scFv was generated.

1.2.1 Amplification and Cloning of the Rodent κ Light Chain Leader Sequence

The signal sequence of a rodent κ light chain was synthesised by overlapping PCR primer containing a Nde I site (gtacaagcttgctagcaagatggaatcacagacccaggtcc, SEQ ID NO:16) and another primer containing a Kpn I site (gtacacgcgttgtaaggact caccccacaggtaccagaaa, SEQ ID NO:17). The κ light chain leader sequence was introduced into the mammalian expression vector pcDNA3.1-zeo (Invitrogen Life Technologies, Karlsruhe, Germany).

1.2.2 Amplification and Cloning of Chicken Constant Regions for scFv-Derived Constructs All chicken immunoglobulin constant domains were synthesised from cDNA derived from chicken splenocytes. The 5' end of the chicken υ heavy chain was amplified using the PCR primer (accgaagtcatcgtctcctc, SEQ ID NO:18) and (cctcagtt tggcgtctaagc, SEQ ID NO:19). The 3' end was amplified using the PCR primer (gaggatcacgtcaagggatg, SEQ ID NO:20) and (gcaccccaatcctttattt, SEQ ID NO:21). After hybridization of these two fragments the complete chicken υ heavy chain was amplified using the PCR primer (accgaagtcatcgtctcctc, SEQ ID NO:18) and (gcaccccaatcctttattt, SEQ ID NO:21).

For the scFv-based homodimeric constructs the chicken υ $C_H$1-4 domain was amplified using one PCR primer containing an Asc I site (gatcggcgcgcccgcgagcccacatcgcc, SEQ ID NO:22) and another PCR primer containing a Xba I site and a 4×His overhang (gatctctagatcagtgatggtgatgtttaccagcctgtttctg, SEQ ID NO:23). The υ $C_H$2-4 domain was amplified using one PCR Primer containing an Asc I site (gatcggcgcgccgcctgtagccccagag, SEQ ID NO:24) and another Primer containing a Xba I site and a 4×His overhang (gatctctagatcagtgatggtgatgtttaccagcctgtttctg, SEQ ID NO:25). The υ $C_H$1-2 domain was amplified using one PCR primer containing an Asc I site (gatcggcgcgcccgcgagccccacatcgcc, SEQ ID NO:26) and another PCR primer containing a Xba I site and a 4×His overhang (gatctctagatcagtgatgtgatggaactccgggcatcccttgacgtgatc, SEQ ID NO:27). The υ $C_H$2 domain was amplified using one PCR primer containing an Asc I site (gatcggcgcgccgcctgtagccccagag, SEQ ID NO:28) and another PCR primer containing a Xba I site and a 4×His overhang (gatctctagatcagtgatggtgatggaactccgggcatcccttgacgtgatc, SEQ ID NO:29). The individual immunoglobulin Fc domains were inserted into the mammalian expression vector pcDNA3.1-zeo (Invitrogen life technologies, Karlsruhe, Germany) containing the rodent κ light chain leader sequence via Asc I and Xba I.

1.2.3 Introduction of the Anti-IBDV scFv Crab15 into the Homodimeric Constructs

Introduction of the anti-IBDV scFv Crab15 into the scFv-$C_H$1-4, the scFv-$C_H$2-4, the scFv-$C_H$1-2 and the scFv-$C_H$2 format was performed by introduction of a BsiW I site at the N-terminus (gatccgtacgtgtggggccgtgacgttggacg, SEQ ID NO:30) and an Asc I site at the C-terminus (gatcggcgcgccac-ctaggacggtcaggg, SEQ ID NO:31) of the antibody fragment by PCR. Subsequently, the DNA was ligated into the vector pcDNA3.1-zeo (Invitrogen life technologies, Karlsruhe, Germany) containing the signal sequence and the particular constant regions.

1.3 Amplification and Cloning of Chimeric Heterotetrameric Antibody Constructs 1.3.1 Amplification and Cloning of Variable Regions of scFv Hyhel10

Transfer of the anti-hen egg lysozyme $V_H$ region into the heterotetrameric IgY was performed by introduction of a Swa I site at the N-terminus (gatcatttaaatgtgtccagtgtgacgtgcagc tgcag, SEQ ID NO:32) and an Asc I site at the C-terminus (gatcggcgcgccgacggtgaccgtggtacc, SEQ ID NO:33) of the antibody fragment by PCR. Transfer of the anti-hen egg lysozyme $V_L$ region into the heterotetrameric antibodies was performed by introduction of a Sbf I site at the N-terminus (gatccctgcagggtgccagatgtgacatcgtgctgacc, SEQ ID NO:34) and an Sgf I site at the C-terminus (gatcgcgatcgctttgatttcct-tcag, SEQ ID NO:35) of the antibody fragment by PCR. Both variable regions were introduced into the mammalian expression vector pBudCE4.1 (Invitrogen life technologies, Karlsruhe, Germany) containing the chicken constant regions and the rodent κ light chain leader sequence via Swa I and Asc I or Sbf I and Sgf I, respectively.

1.3.2 Amplification and Cloning of the ε-υ Chimeric Constant Heavy Chain

The human ε $C_H$1-2 domain was amplified using one PCR primer containing an Asc I site (gatcggcgcgccatccgtcttcccct-tga, SEQ ID NO:36) and another PCR primer containing an υ overlapping region (ggatggggctgcagctctgagcgc-catctgcacacttctt, SEQ ID NO:37). The chicken υ $C_H$3-4 domain was amplified using one PCR primer containing an ε overlapping region (acctttga ggacagcaccaagaagtgtgcagatg-gcgctcagagctgc, SEQ ID NO:38) and another PCR primer containing a Sfi I site and a 4×His overhang (gatcggcccagc-cggcctcagtgatggtgatgtttaccagcctgtt tctg, SEQ ID NO:39). After hybridization of these two fragments the complete chimeric ε-υ heavy chain was amplified using the PCR primer (gatcggcgcgccatccgtcttccccttga, SEQ ID NO:36) and (gatcg-gcccagccggcctcagtgatggtgatgtttaccagcctgttt ctg, SEQ ID NO:39) and was inserted into the mammalian expression vector pBudCE4.1 modified as described above via Asc I and Sfi I.

1.4 Amplification and Cloning of Chimeric Homodimeric Antibody Constructs

1.4.1 Transfer of the anti-hen egg lysozyme scFv into the scFv-$C_H$1-4, the scFv-$C_H$2-4, the scFv-$C_H$1-2 and the scFv-$C_H$2 format was performed by introduction of a BsiW I site at the N-terminus (gatccgtacgtgtggggacgtgcagcttcaggag, SEQ ID NO:40) and an Asc I site at the C-terminus (gatcggcgcgcctt ttatttccagcttggtc, SEQ ID NO:41) of the antibody fragment by PCR. Subsequently, the DNA was ligated into the vector pcDNA3.1-zeo (Invitrogen life technologies, Karlsruhe, Germany) containing the signal sequence and the particular constant regions.

1.5 Amplification and Cloning of Deglycosylated IgY Constructs

The site-directed mutagenesis of the Hyhel-IgY and the Hyhel-IgYΔFc constructs was performed using the QuikChange site-directed mutagenesis kit (Stratagene, La Jolla, USA). For substitution of the glycosylation site in position 407 the mammalian expression vector pBudCE4.1 (Invitrogen life technologies, Karlsruhe, Germany) modified as described above was amplified using the PCR primer (ggtc-ctccaagaacactt ccagggcacctacagcgccagc, SEQ ID NO:42) and the PCR primer (gctggcgctgtaggtgccctggaagt-gtccttggaggacc, SEQ ID NO:43). For substitution of the glycosylation site in position 308 the mammalian expression vector pBudCE4.1 (Invitrogen life technologies, Karlsruhe, Germany) modified as described above was amplified using the PCR primer (gcctgagcagccgcgtcca ggtcagcggcaccgattgg, SEQ ID NO:44) and the PCR primer (ccaatcggtgccgctgac-ctggacgcggctgctcaggc, SEQ ID NO:45). Correctness of the mutations was verified by DNA sequencing.

Example 2

Expression and Purification of Antibody Constructs

For expression of the individual antibody constructs HEK-293 cells (ATCC number CRL-1573) were cultivated in DMEM supplemented with 10% (v/v) heat-inactivated fetal calf serum, 100 IU/ml penicillin, and 100 μg/ml streptomycin. Tissue culture reagents were obtained from Invitrogen life technologies (Karlsruhe, Germany). HEK-293 cells growing in DMEM supplemented with 10% (v/v) fetal calf serum were transfected with 2 μg of the particular expression vector using jetPEI (Qbiogene, Irvine, USA). Stable transfectants then were selected in DMEM supplemented with 10% (v/v) fetal calf serum and 100 μg/ml of zeocin (Invitrogen life technologies, Karlsruhe, Germany).

For protein expression, transfected cells were grown for 3 days as an adhesion culture. The immunoglobulins secreted by transfected HEK-293 cells were purified from the culture medium by affinity chromatography using lysozyme immobilized onto NHS-activated sepharose or Ni-NTA-agarose (Qiagen, Hilden, Germany) according to the manufacturers recommendations. Examples of purified antibody constructs analyzed by Western blot are shown in FIG. 10-12.

Example 3

Immunoreactivity of Antibody Constructs

3.1. Immunoreactivity of the Anti-Hen Egg Lysozyme IgY Constructs

For assessment of immunoreactivity of the anti-hen egg lysozyme constructs purified recombinant proteins (diluted with PBS-milk powder (PBS (2,7 M NaCl, 54 mM KCl, 87 mM Na2HPO4x2H2O, 30 mM KH2PO4), 2% (w/v) milk powder, MPBS) were applied to microtiter plates coated with lysozyme (50 μl per well, 100 μg/ml, Sigma, Taufenstein, Germany) at 4° C. overnight and blocked with MPBS at room temperature for 2 h. After incubation of the microtiter plates for 90 min at room temperature on a rocker platform, the wells were rinsed 3 times each with PBS-Tween (0.1% v/v Tween, TPBS) and PBS and further incubated with 100 μl each of an anti-chicken IgY-HRP (Horseradishperoxidase) conjugate (diluted 1:5000 in 2% (w/v) MPBS, Sigma, Taufenstein, Germany) for 60 min at room temperature on a rocker platform. The wells were rinsed again 3 times each with 0.1% (v/v) TPBS and PBS and bound antibodies were visualised by the addition of 75 μl of an ABTS (2,2'-azino-bis(3-ethylbenzthia-zoline-6-sulfonic acid)) substrate solution (Sigma, Taufenstein, Germany). Absorbance was determined at 405 nm after 20 min of incubation. FIG. 13 shows the immunoreactivity of IgY (complete antibodies and corresponding scFv-derived constructs) with specificity for hen egg lysozyme.

3.2. Immunoreactivity of the Anti-IBDV IgY Constructs

For assessment of immunoreactivity of the anti-IBDV constructs, purified recombinant proteins (diluted with PBS-milk powder (2% (w/v), MPBS) were applied to an nitrocellulose membrane coated with IBDV particles and blocked with MPBS at room temperature for 2 h. After incubation overnight at 4° C. on a rocker platform, the membrane was rinsed 3 times each with PBS-Tween (0.1% v/v, TPBS) and PBS and further incubated with an anti-chicken IgY-AP (Alkaline phosphatase) conjugate (diluted 1:5000 in 2% (w/v) MPBS, Sigma, Taufenstein, Germany) for 60 min at room temperature on a rocker platform. The membrane was rinsed again 3 times each with 0.1% (v/v) TPBS and PBS and bound antibodies were visualised by the addition of an NBT/BCIP (ni-troblue tetrazolium/bromochloroindolyl phosphate) substrate solution (Sigma, Taufenstein, Germany). FIG. 14 shows the immunoreactivity of selected-IgY (complete antibodies and corresponding scFv-derived constructs) with specificity for IBDV.

3.3 Reactivity with Secondary Reagents

For assessment of the reactivity of anti-lysozyme IgY constructs with secondary reagents including anti-chicken IgY- HRP conjugate, ant-human IgG-HRP conjugate and protein A-HRP conjugate, purified recombinant IgY antibody constructs (diluted with PBS-milk powder (2% (w/v), MPBS) were applied to microtiter plates coated with lysozyme (Sigma, Taufenstein, Germany) at 4° C. overnight and blocked with MPBS at room temperature for 2 h. After incubation of the microtiter plates for 90 min at room temperature on a rocker platform, the wells were rinsed 3 times each with PBS-Tween (0.1% v/v, TPBS) and PBS and further incubated with 100 µl each of an Protein A conjugate (diluted 1:100 in 2% (w/v) MPBS, Sigma, Taufenstein, Germany) and as a control with an anti-chicken Ig conjugate (diluted 1:5000 in 2% (w/v) MPBS, Sigma, Taufenstein, Germany) for 60 min at room temperature on a rocker platform. The wells were rinsed again 3 times each with 0.1% (v/v) TPBS and PBS and bound antibodies were visualised by the addition of 75 µl of an ABTS substrate solution (Sigma, Taufenstein, Germany). Absorbance was determined at 405 nm after 20 min of incubation. FIG. 15 shows that IgY (complete antibodies and corresponding scFv-derived constructs) are reactive with anti-chicken IgY-HRP conjugate, but not with ant-human IgG-HRP conjugate or protein A-HRP conjugate Example 4

Evaluation of the Physicochemical Stability of the Antibody Constructs 4.1. Physicochemical Stability of the Antibody Constructs For assessment of the pH stability of chimeric IgY-derived antibody constructs, recombinant human IgG and chimeric IgY, both with specificity for hen egg lysozyme, were incubated under acidic conditions at 37° C. The pH of culture supernatants from IgG and chimeric IgY expressing HEK cells was adjusted to pH 3.0 or 3.5 and the supernatants were incubated for 0 to 60 minutes at 37° C. Thereafter, the supernatants were neutralized and applied to microtiter plates coated with lysozyme (Sigma, Taufenstein, Germany) at 4° C. overnight and blocked with 10% FKS/PBS at room temperature for 2 h. After incubation of the microtiter plates for 90 min at room temperature on a rocker platform, the wells were rinsed 3 times each with PBS-Tween (0.1% v/v, TPBS) and PBS and further incubated with 100 µl each of an anti-chicken IgY-HRP conjugate (diluted 1:5000 in 10% FKS/PBS, Sigma, Taufenstein, Germany) or an anti-human IgG-HRP conjugate (diluted 1:2000 in 10% FKS/PBS, Sigma, Taufenstein, Germany) for 60 min at room temperature on a rocker platform. The wells were rinsed again 3 times each with 0.1% (v/v) TPBS and PBS and bound antibodies were visualised by the addition of 75 µl of an ABTS substrate solution (Sigma, Taufenstein, Germany). Absorbance was determined at 405 nm after 20 min of incubation. FIG. 16 shows that the immunoreactivity of recombinant human IgG and chimeric IgY remains comparable after incubation at pH 3.5 and 3.0. Since native chicken IgY is much less stable under these conditions than mammalian IgG, these data demonstrate that by fusion of mammalian variable domains to IgY constant domains chimeric IgY antibodies can be generated providing mammalian IgG-like pH stability.

Example 5

Lack of Interference of Chimeric Avian Monoclonal Antibodies with RF-Positive Human Serum For assessment of interference of human and avian chimeric monoclonal antibodies with RF the purified recombinant antibodies Hy-IgY (VII) and the human counterpart Hy-huIgG, both with specificity for hen egg lysozyme, were applied to microtiter plates at 4° C. overnight and free binding sites were blocked with FCS (10% v/v in PBS) at room temperature for 30 min. The wells were rinsed one time with PBS and further incubated with 50 µl each of serial dilutions of RF-positive human serum (diluted in 10% FCS v/v in PBS, Scantibodies Laboratories, Villebon/Yvette, France). After incubation for 4 h at room temperature on a rocker platform, the wells were rinsed 2 times with PBS-Tween (0.1% v/v, TPBS) and PBS and further incubated with 50 µl each of either human Ig or rabbit Ig conjugate (huIgG-HRP and raIgG-HRP, both diluted 1:1000 in 10% v/v FCS in PBS, Jackson ImmunoResearch, Soham, UK) for 2 h at room temperature on a rocker platform. The wells were rinsed again 2 times each with 0.1% (v/v) TPBS and PBS and bound antibodies were visualised by the addition of 50 µl of an ABTS substrate solution (Sigma, Taufenstein, Germany). Absorbance was determined at 405 nm after 20 min of incubation. FIG. 17 shows the lack of interference of avian chimeric monoclonal antibodies and the interference of human chimeric monoclonal antibodies with RF, demonstrating the potential of recombinant avian antibodies to avoid false-positive results in immunological assays.

Example 6

Lack of Interference of Chimeric Avian Monoclonal Antibodies with Heterophilic Human Serum For assessment of interference of human and avian chimeric and murin monoclonal antibodies with heterophilic antibodies the purified recombinant antibodies Hy-IgY (VII) and the human and murin counterparts Hy-huIgG and Hy-muIgG, all with specificity for hen egg lysozyme, were applied to microtiter plates at 4° C. overnight and free binding sites were blocked with FCS (10% v/v in PBS) at room temperature for 30 min. The wells were rinsed one time with PBS and further incubated with 50 µl each of serial dilutions of heterophilic human serum (diluted in 10% FCS v/v in PBS, Scantibodies Laboratories, Villebon/Yvette, France). After incubation for 4 h at room temperature on a rocker platform, the wells were rinsed 2 times with PBS-Tween (0.1% v/v, TPBS) and PBS and further incubated with 50 µl each of either human Ig or murin Ig conjugate (huIgG-HRP and muIgG-HRP, both diluted 1:1000 in 10% v/v FCS in PBS, Jackson ImmunoResearch, Soham, UK) for 2 h at room temperature on a rocker platform. The wells were rinsed again 2 times each with 0.1% (v/v) TPBS and PBS and bound antibodies were visualised by the addition of 50 µl of an ABTS substrate solution (Sigma, Taufenstein, Germany). Absorbance was determined at 405 nm after 20 min of incubation. FIG. 18 shows a negligible interference of avian chimeric monoclonal antibodies and the interference of human chimeric monoclonal antibodies with heterophilic antibodies, demonstrating the potential of recombinant avian antibodies to avoid false-positive results in immunological assays.

REFERENCES

Andris-Widhopf J, Rader C, Steinberger P, Fuller R, Barbas 3rd CF. Methods for the generation of chicken monoclonal antibody fragments by phage display. J. Immunol. Meth. 242, 159-181, 2000.

Arbabi Ghahroudi M, Desmyter A, Wyns L, Hamers R, Muyldermans S. Selection and identification of single domain antibody fragments from camel heavy-chain antibodies. FEBS Lett. 414, 521-526, 1997.

Ashikari Y, Arata Y, Hamaguchi K. pH-Induced unfolding of the constant fragment of the immunoglobulin light chain: effect of reduction of the intrachain disulfide bond. J Biochem 97, 517-528, 1985.

Baatrup G, Svehag S E, Jensenius J C. The attachment of serum and plasma derived C3 to solid phase immune aggregates and its relation to complement-mediated solubilization of immune complexes. Scand J Immunol 23, 397-406, 1986.

Barbas 3rd CF, Bain J D, Hoekstra D M, Lerner R A. Semisynthetic combinatorial antibody libraries: a chemical solution to the diversity problem. Proc. Natl. Acad. Sci. U S A, 89, 4457-4461, 1992.

Barbas 3rd CF, Collet A, Amberg W, Roben P, Binley J M, Hoekstra D, Cababa D, Jones T M, Williamson R A, Pilkington G R, et al. Molecular profile of an antibody response to HIV-1 as probed by combinatorial libraries. J. Mol. Bio. 230, 812-823, 1993.

Basu M, Hakimi J, Dharm E, Kondas A J, Tsien W H, Pilson R S, Lin P, Gilfillan A, Haring P, Braswell E H, et al. Purification and characterization of human recombinant IgE-Fc fragments that bind to the human high affinity IgE receptor. J. Biol. Chem. 268, 13118-13127, 1993.

Benkirane R, Gottschalk M, Jaques M, Dubreuil D. Immunochemical characterization of an IgG-binding protein of *Streptococcus* suis. FEMS Immunology and medical microbiology 20, 121-127, 1998.

Blum P M, Phelps D L, Ank B J, Krantman H J, Stiehm E R. Survival of oral human immune serum globulin in the gastrointestinal tract of low birth weight infants. Pediatr Res 15, 1256-1260, 1981.

Bogstedt A K, Hammarstrom L, Robertson A K. Survival of immunoglobulins from different species through the gastrointestinal tract in healthy adult volunteers: implications for human therapy [letter]. Antimicrob Agents Chemother 41, 2320, 1997.

Boscato L, Stuart M. Incidence and Specificity of interference in Two-site immunoassays. Clin chem 32, 1491-1495, 1986.

Boscato L M, Stuart M C. Heterophilic antibodies: a problem for all immunoassays. Clin Chem 34, 27-33, 1988.

Campbell R D, Dodds A W, Porter R R. The binding of human complement component C4 to antibody-antigen aggregates. Biochem J 189, 6780, 1980.

Chambers R E, Whicher J T, Perry D E, Milford-Ward A, White P A, Fifield R. Overestimation of immunoglobulins in the presence of rheumatoid factor by kinetic immunonephelometry and rapid immunoturbidimetry. Ann Clin Biochem 24, 520-524, 1987.

Clackson T, Hoogenboom H R, Griffiths A D, Winter G. Making antibody fragments using phage display libraries. Nature 352, 624-628, 1991.

Copelan E A, Bechtel T P, Klein J P, Klein J L, Tutschka P, Kapoor N, et al. Controlled trial of orally administered immunoglobulin following bone marrow transplantation. Bone Marrow Transplant 13, 87-91, 1994.

Davies E L, Smith J S, Birkett C R, Manser J M, Anderson-Dear D V, Joung J R. Selection of specific phage-display antibodies using libraries derived from chicken immunoglobulin genes. J. Immunol. Meth. 186, 125-135, 1995.

Eibl M M, Wolf H M, Fumkranz H, Rosenkranz A. Prevention of necrotizing enterocolitis in low-birth-weight infants by IgA-IgG feeding. N Engl J Med 319, 1-7, 1988.

Engstrom P E, Larsson A, Norhagen G, Smith C I, Sallberg M, Helgeland K et al. Specificity and levels of oral and systemic antibodies to *Actinobacillus* actinomycetemcomitans. J Clin Periodontol 20, 746-751, 1993.

Faith R E, Clem L W. Passive cutaneous anaphylaxis in the chicken. Biological fractionation of the mediating antibody population. Immunology 25, 151-164, 1973.

Figdor C G, van Kooyk Y, Adema G J. C-Type lectin receptors on dendritic cells and Langerhans cells. Nature Rev. Immunol. 2, 77-84, 2002.

Fischer M, Hlinak A. The lack of binding ability of staphylococcal protein A and streptococcal protein G to egg yolk immunoglobulins of different fowl species (short communication). Berl Munch Tierarztl Wochenschr 113, 94-96, 2000.

Geer L Y, Domrachev M, Lipman D J, Bryant S H. CDART: protein homology by domain architecture. Genome Res. 12:1619-1623, 2002.

Goto Y, Hamaguchi K. The role of the intrachain disulfide bond in the conformation and stability of the constant fragment of the immunoglobulin light chain. J. Biochem. 86, 1433-1441, 1979.

Guss B, Eliasson M, Olsson A, Uhlen M, Frej A K, Jornvall H et al. Structure of the IgG-binding regions of streptococcal protein G. EMBO J 5, 1567-1575, 1986.

Hendershot L, Bole D, Kohler G, Kearney J F. Assembly and secretion of heavy chains that do not associate posttranslationally with immunoglobulin heavy chain-binding protein. J. Cell Biol. 104, 761-767, 1987.

Hendershot L, Wei J, Gaut J, et al. Inhibition of immunoglobulin folding and secretion of dominant negative Bip AtPase mutants. Proc. Natl. Acad. Sci. USA 93, 5269-5274, 1996.

Hendershot L A. The ER chaperone BiP is a master regulator of ER Function. Mount Sinai J. Med. 71, 289-297, 2004.

Hilpert H, Brussow H, Mietens C, Sidoti J, Lerner L, Werchau H. Use of bovine milk concentrate containing antibody to rotavirus to treat rotavirus gastroenteritis in infants. J Infect Dis 156, 158-166, 1987.

Hoffman W L, Ruggles A O, Tabarya D. Chicken anti-protein A prevents *Staphylococcus aureus* protein A from binding to human and rabbit IgG in immunoassays and eliminates most false positive results. J Immunol Methods 198, 67-77, 1996.

Holliger P, Prospero, T, Winter G. 'Diabodies': small bivalent and bispecific antibody fragments. Proc. Natl. Acad. Sci. USA 90, 6444, 1993.

Hoogenboom, H. R., Winter, G. By-passing immunisation. Human antibodies from syntheticrepertoires of germline VH gene segments rearranged in vitro. J. Mol. Biol. 227, 381-388, 1992.

Horton J, Holden C, Ward P, MacDonald D, Sanderson A. Exploitation of phylogenetic distance in cell surface immune labeling: studies with Beta$_2$-microglobulin. J Invest Dermatol 85, 96-99, 1984.

Johnson P M, Faulk W P. Rheumatoid factor: its nature, specificity, and production in rheumatoid arthritis. Clin Immunol Immunopathol 6, 414-430, 1976.

Kapyaho K, Tanner P, Weber T. Effect of complement binding on a solidphase immunometric TSH assay. Scand J Clin Lab Invest 49, 211215, 1989.

Kastern W, Holst E, Nielsen E, Sjobring U, Bjorck L. Protein L, a bacterial immunoglobulin-binding protein and possible virulence determinant. Infect Immun 58, 1217-1222, 1990.

Kelly C P, Chetham S, Keates S, Bostwick E F, Roush A M, Castagliuolo I et al.: Survival of anti-*Clostridium difficile* bovine immunoglobulin concentrate in the human gastrointestinal tract. Antimicrob Agents Chemother 41, 236-241, 1997.

Knittler M R, Haas I G. Interaction of BiP with newly synthesized immunoglobulin light chain molecules: cycles of sequential binding and release. EMBO J. 11, 1573-1581, 1992.

Kollberg H, Carlander D, Olesen H., Wejaker P E, Johannesson M, Larsson A. Oral administration of specific yolk antibodies (IgY) may prevent *Pseudomonas aeruginosa* infections in patients with cystic fibrosis: a phase I feasibility study. Pediatr. Pulmonol. 35, 433-440, 2003.

Kricka L J. Human anti-animal antibody interferences in immunological assays. Clin Chem 45, 942-956, 1999.

Krüger C, Pearson, S K, Kodama Y, Vacca Smith B, Bowen W H, Hammarstroöm L. The effects of egg-derived antibodies to glucosyltransferases on dental carries in rats. Carries Res. 38, 9-14, 2004.

Lang I M, Barbas 3rd C F, Schleef R R. Recombinant rabbit Fab with binding activity to type-1 plasminogen activator inhibitor derived from a phage-display library against human alpha-granules. Gene 172, 295-298, 1996.

Larsson A, Sjoquist J. Binding of complement components C1q, C3, C4 and C5 to a model immune complex in ELISA. J Immunol Methods 119, 103-109, 1989.

Larsson A, Karlsson-Parra A, Sjoquist J. Use of chicken antibodies in enzyme immunoassays to avoid interference by rheumatoid factors. Clin Chem 37, 411-414, 1991.

Larsson A, Mellstedt H. Chicken antibodies: a tool to avoid interference by human anti-mouse antibodies in ELISA after in vivo treatment with murine monoclonal antibodies. Hybridoma 11, 33-39, 1992.

Larsson A, Wejaker P E, Forsberg P O, Lindahl T. Chicken antibodies: a tool to avoid interference by complement activation in ELISA. J Immunol Methods 156, 79-83, 1992.

Larsson A, Lindahl T. Chicken antibodies: a tool to avoid interference in immunological assays. Avian immunology in progress; Ed. INRA Paris 1993, 97-102, 1993.

Leslie G A, Clem L W. Phylogen of immunoglobulin structure and function. Immunoglobulins of the chicken. J Exp Med 130, 1337-1352, 1969.

Lindahl T L, Festin R, Larsson A. Studies of fibrinogen binding to platelets by flow cytometry: an improved method for studies of platelet activation. Thromb Haemost 68, 221-225, 1992.

Losonsky G A, Johnson J P, Winkelstein J A, Yolken R H. Oral administration of human serum immunoglobulin in immunodeficient patients with viral gastroenteritis. A pharmacokinetic and functional analysis. J Clin Invest 76, 2362-2367, 1985.

Malhotra R., Wormald M R, Rudd P M, Fischer P B, Dwek R A, Sim R B. Glycosylation changes of IgG associated with rheumatoid arthritis can activate complement via the mannose-binding protein. Nat. Med. 1, 237-243, 1995

Marks J D, Hoogenboom H R, Bonnert T P, McCafferty J, Griffiths A D, Winter G. By-passing immunization. Human antibodies from V-gene libraries displayed on phage. J. Mol. Biol. 222, 581-597, 1991.

Matsuda H, Mitsuda H, Nakamura N, Furusawa S, Mori S, Kitamoto T. A chicken monoclonal antibody with specificity for the N-terminal of human prion protein. FEMS Immunol. Med. Microbiol. 23, 189, 1999.

Miller G W, Nussenzweig V. A new complement function: solubilization of antigen-antibody aggregates. Proc Natl Acad Sci USA 72, 418422, 1975.

Mine, Y., Kovacs-Nolan, J. Chicken egg yolk antibodies as therapeutics in enteric infectious diseases: a review. J. Med. Food 5, 159-169, 2002.

Nakamura N, Shimokawa M, Miyamoto K, Hojyo S, Horiuchi H, Furusawa S, Matsuda H. Two expression vectors for the phage-displayed chicken monoclonal antibody. J. Immunol. Meth. 280, 157-164, 2003.

Nishinaka S, Matsuda H, Murata M. Establishment of a chicken X chicken hybridoma secreting specific antibody. Int. Arch. Allergy Appl. Immunol. 89, 416-419, 1989.

Nishinaka S, Suzuki T, Matsuda H, Murata M. A new cell line for the production of chicken monoclonal antibody by hybridoma technology. J Immunol. Methods 139, 217-222, 1991.

Nishinaka S, Akiba H, Nakamura M, Suzuki K, Suzuki T, Tsubokura K, Horiuchi H, Furusawa S, Matsuda H. Two chicken B cell lines resistant to ouabain for the production of chicken monoclonal antibodies. J. Vet. Med. Sci. 58, 1053-1056, 1996.

Nissim A, Hoogenboom H R, Tomlinson I M, Flynn G, Midgley C, Lane D, Winter G. Antibody fragments from a 'single pot' phage display library as immunochemical reagents. EMBO J. 13, 692-698, 1994.

Ohtani H, Matsumoto K, Saeki A, Hosono, A. Comparative studies on properties of hen egg yolk IgY and rabbit serum IgG antibodies. Lebensm. Wiss. Technol. 24, 152-158, 1991.

Olovsson M, Larsson A. Biotin labelling of chicken antibodies and their subsequent use in ELISA and immunohistochemistry. Comp Immunol Microbiol Infect Dis 16, 145-152, 1993.

Parvari R, Avivi A, Lentner F, Ziv E, Tel-Or S, Burstein Y, Schechter I. Chicken immunoglobulin γ-heavy chains: limited VH gene repertoire, combinatorial diversification by D gene segments and evolution of the heavy chain locus. EMBO J. 7, 739-744, 1988.

Parvari R, Ziv E, Lentner F, Heller D, Schechter I. Somatic diversification of chicken immunoglobulin light chains by point mutations. Proc. Natl. Acad. Sci. USA 87, 3072-3076, 1990.

Polson A. Manufacture and use of fowl egg antibodies. U.S. Pat. No. 4,550,019, October 1985.

Ramirez A D, Rocha E M, Krettli A U. Antisporozoite antibodies with protective and non-protective activities: in vitro and in vivo correlations using *Plasmodium gallinaceum*, an avian model. J. Eukaryot. Microbiol. 42, 705-708, 1995.

Reilly R M, Domingo R, Sandhu J. Oral delivery of antibodies. Future pharmacokinetic trends. Clin Pharmacokinet 32, 313-323, 1997.

Roos A, Bouwman L H, van Gijlswijk-Janssen D J, Faber-Krol M C, Fallaux-van den Houten F C, Klar-Mohamad N, Hack C E, Tilanus M G, Daha M R. Human IgA activates the complement system via the mannan-binding lectin pathway. J. Immunol. 167, 2861-2868, 2001.

Rubinstein E, Kouns W C, Jennings L K, Boucheix C, Carroll R C. Interaction of two GPIIb/IIIa monoclonal antibodies with platelet Fc receptor (Fc gamma RII). Br J Haematol 78, 80-86, 1991.

Sambrook J, Fritsch E F, Maniatis T. Molecular Cloning. A Laboratory Manual, second ed., Cold Spring Harbor Press, 1989.

Sapats S I, Heine H G, Trinidad L, Gould G J, Foord A J, Doolan S G, Prowse S, Ignjatovic J. Generation of chicken single chain antibody variable fragments (scFv) that differentiate and neutralize infectious bursal disease virus (IBDV). Arch. Virol. 148, 497-515, 2003.

Shimizu M, Nagashima H, Sano K, Hashimoto K, Ozeki M, Tsuda K, Hatta H. Molecular stability of chicken and rabbit immunoglobulin G. Biosci Biotechnol Biochem 56, 270-274, 1992.

Smith D J, King W F, Godiska R. Passive transfer of immunoglobulin Y antibody to *Streptococcus mutans* glucan binding protein B can confer protection against experimental dental carries. Infect. Immun. 69, 3135-3142, 2001.

Song C S, Yu J H, Bai D H, Hester P Y, Kim K H. Antibodies to the alphasubunit of insulin receptor from eggs of immunized hens. J Immunol 135, 3354-3359, 1985.

Sun S, Mo W, Il Y, Liu S. Preparation and mass spectrometric study of egg yolk antibody (IgY) against rabies virus. Rapid Commun Mass Spectrom 15, 708-712, 2001.

Suzuki N, Khoo K H, Chen C M, Chen C H, Lee Y C. N-glycan structures of pigeon IgG: a major serum glycoprotein containing Galα1-4Gal termini J. Biol. Chem. 278, 46293-46306, 2003.

Suzuki N, Lee Y C. Site-specific N-glycosylation of chicken serum IgG. Glycobiology 14, 275-292, 2004.

Takahashi N, Nakagawa H, Fujikawa K, Kawamura Y, Tomiya N. Three-dimensional elution mapping of pyridylaminated N-linked neutral and sialyl oligosaccharides. Anal. Biochem. 226, 139-146, 1995.

Van de Wetering J K., van Golde L M G, Batenburg J J. Collectins. Players of thevinnate immune system. Eur. J. Biochem. 271, 1229-1249, 2004.

Van de Winkel J G, Capel P J. Human IgG Fc receptor heterogeneity: molecular aspects and clinical implications. Immunol Today 14, 215-221, 1993.

Van Dijk M A, van de Winkel J G J. Human antibodies as next generation therapeutics. Curr. Opin. Chem. Biol. 5, 368-374, 2001.

Wan T, Beavil R L, Fabiane S M, Beavil A J, Sohi M K, Keown M, Young R J, Henry A J, Owens R J, Gould H J, Sutton B J. The crystal structure of IgE Fc reveals an asymmetrically bent conformation. Nat. Immunol. 3, 681-686, 2002.

Warr G W, Magor K E, Higgins D A. IgY: clues to the origins of modern antibodies. Immunol Today 16, 392-398, 1995.

Whaley, K. Measurement of complement. In Methods in complement for clinical immunologists (K. Whaley, ed.), p. 77-139. Churchill Livingstone, Edinburgh, United Kingdom, 1985.

Yamanaka H I, Inoue T, Ikeda-Tanaka O. Chicken monoclonal antibodyisolated by a phage display system. J. Immunol. 157, 1156-1162, 1996.

The invention claimed is:

1. A chimeric bivalent antigen-binding antibody construct comprising at least one avian constant domain selected from the group consisting of $C_H2$ and $C_H3$ avian IgY domains, wherein the Fc region of the chimeric antibody does not comprise a $C_H4$ domain, and wherein the variable domains are of non-avian origin.

2. The antibody construct of claim 1, wherein the carboxy-terminal heavy chain domain is an avian domain.

3. The antibody construct of claim 1 comprising $V_L$, $V_H$, and $C_H2$-domains.

4. The antibody construct of claim 3, further comprising at least one domain selected from the group consisting of $C_H1$, $C_H1$ and $C_L$, and $C_H3$.

5. The antibody construct of claim 3, not comprising a $C_H3$ domain, wherein the construct comprises the additional amino acids EF at the carboxy terminal end of the $C_H2$ domain.

6. The antibody construct of claim 1, wherein $V_H$, $V_L$, $C_L$, and $C_H1$ domains as well as the hinge region are independently of avian or non-avian origin.

7. The antibody construct of claim 1 comprising $V_H$, $V_L$, $C_L$, $C_H1$, and $C_H2$ domains, wherein the $V_H$, $V_L$, $C_L$, and $C_H1$ domains as well as the hinge region are of mammalian origin.

8. The antibody construct of claim 1, wherein all constant domains are avian constant domains.

9. The antibody construct of claim 1, wherein the variable domains are scFv.

10. The antibody construct of claim 1, wherein the avian domains are of chicken or duck origin or chicken-duck chimeric origin.

11. The antibody construct of any of claims 6 or 7, wherein the non-avian origin is mammalian origin.

12. The antibody construct of claim 1, which is expressed in mammalian cells.

13. The antibody construct of claim 1, wherein one or more glycosylation sites are deleted.

14. The antibody construct of claim 1, which is homodimeric or heterotetrameric.

15. A diagnostic agent comprising the antibody construct of claim 1.

16. A pharmaceutical composition comprising the antibody construct of claim 1.

17. The pharmaceutical composition of claim 16, wherein the composition is for peroral administration.

18. A chimeric bivalent antigen-binding antibody construct comprising at least one avian constant domain selected from the group consisting of $C_H2$ IgY domain, $C_H3$ IgY domain, and $C_H4$ IgY domain, comprising $V_L$, $V_H$ and $C_H2$ domains, wherein the variable domains are of non-avian origin, and wherein the $C_H1$ domain is deleted.

19. A pharmaceutical composition comprising the antibody construct of claim 18.

20. A chimeric bivalent antigen-binding antibody construct comprising a chicken $C_H2$ IgY domain and further comprising $V_H$ and $V_L$ domains, and not comprising $C_H3$ and $C_H4$ domains, wherein the construct comprises the additional amino acids EF at the carboxyterminal end of the $C_H2$ domain, and wherein the variable domains are of non-avian origin.

21. A pharmaceutical composition comprising the antibody construct of claim 20.

22. The pharmaceutical composition of claim 21, wherein the composition is for peroral administration.

23. The chimeric antibody of claim 1, wherein the CH1 domain is an avian IgY domain.

* * * * *

```
                         SEQUENCE LISTING

<160> NUMBER OF SEQ ID NOS: 49

<210> SEQ ID NO 1
<211> LENGTH: 57
<212> TYPE: DNA
<213> ORGANISM: Artificial Sequence
<220> FEATURE:
<223> OTHER INFORMATION: Primer

<400> SEQUENCE: 1
ctggggctcc tgctactctg cctgcagggt gccagatgtg cgctgactca gccgtcc        57

<210> SEQ ID NO 2
<211> LENGTH: 55
<212> TYPE: DNA
<213> ORGANISM: Artificial Sequence
<220> FEATURE:
<223> OTHER INFORMATION: Primer

<400> SEQUENCE: 2
gatcgtcgac atggacatga gggtccccgc tcagctcctg gggctcctgc tactc          55

<210> SEQ ID NO 3
<211> LENGTH: 36
<212> TYPE: DNA
<213> ORGANISM: Artificial Sequence
<220> FEATURE:
<223> OTHER INFORMATION: Primer

<400> SEQUENCE: 3
gatcgcgatc gcacctagga cggtcagggt tgtccc                               36

<210> SEQ ID NO 4
<211> LENGTH: 48
<212> TYPE: DNA
<213> ORGANISM: Artificial Sequence
<220> FEATURE:
<223> OTHER INFORMATION: Primer
```

<400> SEQUENCE: 4 tgggtttttcc ttgttgctag gcgcgccatc tagagaggag acgatgac                48

<210> SEQ ID NO 5
<211> LENGTH: 48
<212> TYPE: DNA
<213> ORGANISM: Artificial Sequence
<220> FEATURE:
<223> OTHER INFORMATION: Primer

<400> SEQUENCE: 5
agaatgcggc cgcatggaat tggggctgag ctgggttttc cttgttgc                 48

<210> SEQ ID NO 6
<211> LENGTH: 33
<212> TYPE: DNA
<213> ORGANISM: Artificial Sequence
<220> FEATURE:
<223> OTHER INFORMATION: Primer

<400> SEQUENCE: 6
gatcggcgcg ccagaggaga cgatgacttc ggt                                 33

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
accgaagtca tcgtctcctc                                                20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
cctcagtttg gcgtctaagc                                                20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
gaggatcacg tcaagggatg                                                20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gcacccccaa tcctttattt                                                20

<210> SEQ ID NO 11
<211> LENGTH: 30

```
<212> TYPE: DNA
<213> ORGANISM: Artificial Sequence
<220> FEATURE:
<223> OTHER INFORMATION: Primer

<400> SEQUENCE: 11
gatcggcgcg cccgcgagcc ccacatcgcc                                    30

<210> SEQ ID NO 12
<211> LENGTH: 50
<212> TYPE: DNA
<213> ORGANISM: Artificial Sequence
<220> FEATURE:
<223> OTHER INFORMATION: Primer

<400> SEQUENCE: 12
gatcggccca gccggcctca gtgatggtga tgtttaccag cctgtttctg              50

<210> SEQ ID NO 13
<211> LENGTH: 59
<212> TYPE: DNA
<213> ORGANISM: Artificial Sequence
<220> FEATURE:
<223> OTHER INFORMATION: Primer

<400> SEQUENCE: 13
gatcggccca gccggcctca gtgatggtga tggaactccg ggcatccctt gacgtgatc    59

<210> SEQ ID NO 14
<211> LENGTH: 33
<212> TYPE: DNA
<213> ORGANISM: Artificial Sequence
<220> FEATURE:
<223> OTHER INFORMATION: Primer

<400> SEQUENCE: 14
gatcgcgatc gcgcagccca aggtggcccc cac                                33

<210> SEQ ID NO 15
<211> LENGTH: 31
<212> TYPE: DNA
<213> ORGANISM: Artificial Sequence
<220> FEATURE:
<223> OTHER INFORMATION: Primer

<400> SEQUENCE: 15
gatctctaga tcagcactcg gacctcttca g                                  31

<210> SEQ ID NO 16
<211> LENGTH: 41
<212> TYPE: DNA
<213> ORGANISM: Artificial Sequence
<220> FEATURE:
<223> OTHER INFORMATION: Primer

<400> SEQUENCE: 16
gtacaagctt gctagcaaga tggaatcaca gacccaggtc c                       41

<210> SEQ ID NO 17
<211> LENGTH: 40
<212> TYPE: DNA
<213> ORGANISM: Artificial Sequence
<220> FEATURE:
<223> OTHER INFORMATION: Primer

<400> SEQUENCE: 17
```

```
gtacacgcgt tgtaaggact caccccacag gtaccagaaa                            40
```

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18

```
accgaagtca tcgtctcctc                                                  20
```

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19

```
cctcagtttg gcgtctaagc                                                  20
```

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20

```
gaggatcacg tcaagggatg                                                  20
```

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21

```
gcaccccaa tcctttattt                                                   20
```

<210> SEQ ID NO 22
<211> LENGTH: 30
<212> TYPE: DNA
<213> ORGANISM: Artificial Sequence
<220> FEATURE:
<223> OTHER INFORMATION: Primer

<400> SEQUENCE: 22

```
gatcggcgcg cccgcgagcc ccacatcgcc                                       30
```

<210> SEQ ID NO 23
<211> LENGTH: 43
<212> TYPE: DNA
<213> ORGANISM: Artificial Sequence
<220> FEATURE:
<223> OTHER INFORMATION: Primer

<400> SEQUENCE: 23

```
gatctctaga tcagtgatgg tgatgtttac cagcctgttt ctg                        43
```

<210> SEQ ID NO 24
<211> LENGTH: 28
<212> TYPE: DNA
<213> ORGANISM: Artificial Sequence

```
<220> FEATURE:
<223> OTHER INFORMATION: Primer

<400> SEQUENCE: 24
gatcggcgcg ccgcctgtag ccccagag                                           28

<210> SEQ ID NO 25
<211> LENGTH: 43
<212> TYPE: DNA
<213> ORGANISM: Artificial Sequence
<220> FEATURE:
<223> OTHER INFORMATION: Primer

<400> SEQUENCE: 25
gatctctaga tcagtgatgg tgatgtttac cagcctgttt ctg                          43

<210> SEQ ID NO 26
<211> LENGTH: 30
<212> TYPE: DNA
<213> ORGANISM: Artificial Sequence
<220> FEATURE:
<223> OTHER INFORMATION: Primer

<400> SEQUENCE: 26
gatcggcgcg cccgcgagcc ccacatcgcc                                         30

<210> SEQ ID NO 27
<211> LENGTH: 52
<212> TYPE: DNA
<213> ORGANISM: Artificial Sequence
<220> FEATURE:
<223> OTHER INFORMATION: Primer

<400> SEQUENCE: 27
gatctctaga tcagtgatgg tgatggaact ccgggcatcc cttgacgtga tc                52

<210> SEQ ID NO 28
<211> LENGTH: 28
<212> TYPE: DNA
<213> ORGANISM: Artificial Sequence
<220> FEATURE:
<223> OTHER INFORMATION: Primer

<400> SEQUENCE: 28
gatcggcgcg ccgcctgtag ccccagag                                           28

<210> SEQ ID NO 29
<211> LENGTH: 52
<212> TYPE: DNA
<213> ORGANISM: Artificial Sequence
<220> FEATURE:
<223> OTHER INFORMATION: Primer

<400> SEQUENCE: 29
gatctctaga tcagtgatgg tgatggaact ccgggcatcc cttgacgtga tc                52

<210> SEQ ID NO 30
<211> LENGTH: 32
<212> TYPE: DNA
<213> ORGANISM: Artificial Sequence
<220> FEATURE:
<223> OTHER INFORMATION: Primer

<400> SEQUENCE: 30
gatccgtacg tgtggggccg tgacgttgga cg                                      32
```

```
<210> SEQ ID NO 31
<211> LENGTH: 29
<212> TYPE: DNA
<213> ORGANISM: Artificial Sequence
<220> FEATURE:
<223> OTHER INFORMATION: Primer

<400> SEQUENCE: 31
gatcggcgcg ccacctagga cggtcaggg                                    29

<210> SEQ ID NO 32
<211> LENGTH: 38
<212> TYPE: DNA
<213> ORGANISM: Artificial Sequence
<220> FEATURE:
<223> OTHER INFORMATION: Primer

<400> SEQUENCE: 32
gatcatttaa atgtgtccag tgtgacgtgc agctgcag                          38

<210> SEQ ID NO 33
<211> LENGTH: 30
<212> TYPE: DNA
<213> ORGANISM: Artificial Sequence
<220> FEATURE:
<223> OTHER INFORMATION: Primer

<400> SEQUENCE: 33
gatcggcgcg ccgacggtga ccgtggtacc                                   30

<210> SEQ ID NO 34
<211> LENGTH: 38
<212> TYPE: DNA
<213> ORGANISM: Artificial Sequence
<220> FEATURE:
<223> OTHER INFORMATION: Primer

<400> SEQUENCE: 34
gatccctgca gggtgccaga tgtgacatcg tgctgacc                          38

<210> SEQ ID NO 35
<211> LENGTH: 27
<212> TYPE: DNA
<213> ORGANISM: Artificial Sequence
<220> FEATURE:
<223> OTHER INFORMATION: Primer

<400> SEQUENCE: 35
gatcgcgatc gctttgattt ccttcag                                      27

<210> SEQ ID NO 36
<211> LENGTH: 29
<212> TYPE: DNA
<213> ORGANISM: Artificial Sequence
<220> FEATURE:
<223> OTHER INFORMATION: Primer

<400> SEQUENCE: 36
gatcggcgcg ccatccgtct tccccttga                                    29

<210> SEQ ID NO 37
<211> LENGTH: 40
<212> TYPE: DNA
<213> ORGANISM: Artificial Sequence
<220> FEATURE:
<223> OTHER INFORMATION: Primer
```

<400> SEQUENCE: 37
ggatggggct gcagctctga gcgccatctg cacacttctt    40

<210> SEQ ID NO 38
<211> LENGTH: 48
<212> TYPE: DNA
<213> ORGANISM: Artificial Sequence
<220> FEATURE:
<223> OTHER INFORMATION: Primer

<400> SEQUENCE: 38
acctttgagg acagcaccaa gaagtgtgca gatggcgctc agagctgc    48

<210> SEQ ID NO 39
<211> LENGTH: 50
<212> TYPE: DNA
<213> ORGANISM: Artificial Sequence
<220> FEATURE:
<223> OTHER INFORMATION: Primer

<400> SEQUENCE: 39
gatcggccca gccggcctca gtgatggtga tgtttaccag cctgtttctg    50

<210> SEQ ID NO 40
<211> LENGTH: 34
<212> TYPE: DNA
<213> ORGANISM: Artificial Sequence
<220> FEATURE:
<223> OTHER INFORMATION: Primer

<400> SEQUENCE: 40
gatccgtacg tgtgggacg tgcagcttca ggag    34

<210> SEQ ID NO 41
<211> LENGTH: 31
<212> TYPE: DNA
<213> ORGANISM: Artificial Sequence
<220> FEATURE:
<223> OTHER INFORMATION: Primer

<400> SEQUENCE: 41
gatcggcgcg cctttattt ccagcttggt c    31

<210> SEQ ID NO 42
<211> LENGTH: 40
<212> TYPE: DNA
<213> ORGANISM: Artificial Sequence
<220> FEATURE:
<223> OTHER INFORMATION: Primer

<400> SEQUENCE: 42
ggtcctccaa gaacacttcc agggcaccta cagcgccagc    40

<210> SEQ ID NO 43
<211> LENGTH: 40
<212> TYPE: DNA
<213> ORGANISM: Artificial Sequence
<220> FEATURE:
<223> OTHER INFORMATION: Primer

<400> SEQUENCE: 43
gctggcgctg taggtgccct ggaagtgtcc ttggaggacc    40

<210> SEQ ID NO 44

```
<211> LENGTH: 38
<212> TYPE: DNA
<213> ORGANISM: Artificial Sequence
<220> FEATURE:
<223> OTHER INFORMATION: Primer

<400> SEQUENCE: 44
gcctgagcag ccgcgtccag gtcagcggca ccgattgg        38

<210> SEQ ID NO 45
<211> LENGTH: 38
<212> TYPE: DNA
<213> ORGANISM: Artificial Sequence
<220> FEATURE:
<223> OTHER INFORMATION: Primer

<400> SEQUENCE: 45
ccaatcggtg ccgctgacct ggacgcggct gctcaggc        38

<210> SEQ ID NO 46
<211> LENGTH: 103
<212> TYPE: PRT
<213> ORGANISM: Gallus gallus

<400> SEQUENCE: 46

Ser Pro Thr Ser Pro Arg Leu Tyr Pro Leu Ser Ala Cys Cys Ser
1               5                   10                  15

Asp Ser Ala Val Pro Pro Ala Val Gly Cys Leu Leu Ser Pro Ser Ser
                20                  25                  30

Ala Gly Gly Ile Ser Trp Glu Gly Ser Gly Thr Ala Val Ala Gly
            35                  40                  45

Arg Val Ser Gly Thr Pro Val Lys Leu Ser Phe Val Arg Leu Ser Pro
    50                  55                  60

Gly Glu Lys Arg Lys Ser Phe Val Cys Ser Ala Ala Pro Gly Gly Ala
65                  70                  75                  80

Leu Leu Lys Lys Glu Val Gln Val Cys Arg Val Asp Pro Val Pro Pro
                85                  90                  95

Val Ala Pro Glu Val Gln Val
            100

<210> SEQ ID NO 47
<211> LENGTH: 120
<212> TYPE: PRT
<213> ORGANISM: Homo sapiens

<400> SEQUENCE: 47

Val Ser Ser Ala Ser Thr Lys Gly Pro Ser Val Phe Pro Leu Ala Pro
1               5                   10                  15

Ser Ser Lys Ser Thr Ser Gly Gly Thr Ala Ala Leu Gly Cys Leu Val
                20                  25                  30

Lys Asp Tyr Phe Pro Glu Pro Val Thr Val Ser Trp Asn Ser Gly Ala
            35                  40                  45

Leu Thr Ser Gly Val His Thr Phe Pro Ala Val Leu Gln Ser Ser Gly
    50                  55                  60

Leu Tyr Ser Leu Ser Ser Val Val Thr Val Pro Ser Ser Ser Leu Gly
65                  70                  75                  80

Thr Gln Thr Tyr Ile Cys Asn Val Asn His Lys Pro Ser Asn Thr Lys
                85                  90                  95

Val Asp Lys Lys Val Glu Pro Lys Ser Cys Asp Lys Thr His Thr Cys
            100                 105                 110
```

```
Pro Pro Cys Pro Ala Pro Glu Leu
        115                 120

<210> SEQ ID NO 48
<211> LENGTH: 312
<212> TYPE: DNA
<213> ORGANISM: Gallus gallus

<400> SEQUENCE: 48
cagcccaagg tggccccac catcaccctc ttcccaccgt caaaggagga gctgaacgaa      60
gccaccaagg ccaccctggt gtgcctgata aacgacttct accccagccc agtgactgtg     120
gattgggtga tcgatggctc cacccgctct ggcgagacca cagcaccaca gcggcagagc    180
aacagccagt atatggccag cagctatctg tcactgtctg ccagcgactg gtcaagccac    240
gagacctaca cctgcagggt cacacacgac ggcacctcta tcacgaagac cctgaagagg    300
tccgagtgct aa                                                         312

<210> SEQ ID NO 49
<211> LENGTH: 1282
<212> TYPE: DNA
<213> ORGANISM: Gallus gallus

<400> SEQUENCE: 49
cgcgagcccc acatcgcccc cccgattgta ccctctatcc gcctgttgtt ccgactcggc      60
tgtcccgccg gccgtgggct gcctgttgtc cccttcgtcc gccggcggca tctcctggga     120
gggctccgga ggtacggcgg tggccggcag agtttcgggg accccgtga agctcagctt     180 cgtccgcctc agccccggcg agaagaggaa aagcttcgtc tgcagcgccg ccccgggg     240 ggcgctgctc aaaaaggagg tgcaggtctg ccgggtagat cccgtaccgc ctgtagcccc    300
agaggtgcag gtcctccacc cctcctcctg caccccgagc caatccgagt cggtggagct    360
gttgtgtttg gtgacggggt tctccccggc gtcggcggag tcgaatggt tggtggacgg     420 agtgggggga cttttggtgg cctcccaaag cccggcggtc cgcagcggat ccacctacag    480
cctgagcagc gcgtcaacg tcagcggcac cgattggagg gaagggaaga gttacagctg     540
tagggtgagg caccccgcaa ccaacaccgt ggtggaggat cacgtcaagg gatgcccgga    600
cggcgctcag agctgcagcc ccatccagct gtacgccatc ccacccagcc cgggcgagct    660
gtacatcagc ttagacgcca aactgaggtg cctggtggtc aacctgccca gcgattccag    720
cctcagcgtc acctggacca gggagaagag tgggaacctc cggcccgacc cgatggtcct    780
ccaagaacac ttcaacggca cctacagcgc cagcagcgcc gtcccccgtca gcacccagga    840 ttggttatcc ggggagaggt tcacctgcac cgtgcagcac gaggagctgc ccctgccgct    900
cagcaagagc gtctacagga acacgggacc caccaccca cctctgatct accccttcgc    960 cccccaccccg aagagctgt ccctctcccg cgtcaccctg agctgcctgg tccgcggctt   1020
ccgcccacgt gacatcgaga tccggtggct ccgcgaccac cgcgccgttc ccgccaccga   1080
attcgtcacc accgccgtcc tcccggaaga gagaaccgca acggcgccg gcggtgacgg    1140 cgacaccttc ttcgtgtaca gtaagatgag cgtggagacc gccaagtgga acggcgggac    1200
ggtgttcgcc tgcatggcgg tgcacgaggc gctgcccatg cgcttcagcc agcgcacgct    1260
gcagaaacag gctggtaaat aa                                             1282
```